(12) United States Patent
Wu et al.

(10) Patent No.: US 8,293,231 B2
(45) Date of Patent: Oct. 23, 2012

(54) METHODS AND COMPOSITIONS FOR TREATING ISCHEMIA

(75) Inventors: Hua-Lin Wu, Tainan (TW); Guey-Yueh Shi, Tainan (TW)

(73) Assignee: Blue Blood Biotech Corp., Taipei (TW)

( * ) Notice: Subject to any disclaimer, the term of this patent is extended or adjusted under 35 U.S.C. 154(b) by 220 days.

(21) Appl. No.: 12/856,556

(22) Filed: Aug. 13, 2010

(65) Prior Publication Data

US 2010/0303800 A1      Dec. 2, 2010

Related U.S. Application Data

(60) Division of application No. 12/316,194, filed on Dec. 10, 2008, now Pat. No. 7,803,367, which is a continuation of application No. 11/149,378, filed on Jun. 9, 2005, now abandoned.

(60) Provisional application No. 60/641,213, filed on Jan. 3, 2005.

(51) Int. Cl.
    *A61K 38/48*          (2006.01)

(52) U.S. Cl. ........ 424/94.64; 424/94.3; 514/12; 530/350
(58) Field of Classification Search .................. None
    See application file for complete search history.

(56) References Cited

U.S. PATENT DOCUMENTS

| | | | |
|---|---|---|---|
| 5,476,862 A * | 12/1995 | Calnek et al. .................. 514/324 |
| 5,583,102 A | 12/1996 | Lentz et al. | |
| 5,700,815 A * | 12/1997 | Calnek et al. .................. 514/324 |
| 7,067,649 B2 * | 6/2006 | Harats ........................... 536/24.1 |
| 7,341,992 B2 * | 3/2008 | Conway et al. ............... 514/15.1 |
| 7,579,327 B2 * | 8/2009 | Harats et al. ................. 514/44 R |
| 7,803,367 B2 * | 9/2010 | Wu et al. ....................... 424/94.3 |
| 8,128,963 B2 * | 3/2012 | Pinsky et al. .................. 424/699 |

* cited by examiner

*Primary Examiner* — Hope Robinson
(74) *Attorney, Agent, or Firm* — Hsiu-Ming Saunders; Intellectual Property Connections, Inc.

(57) ABSTRACT

A method for treating ischemia that would benefit from angiogenesis is disclosed. The method comprises administering to a subject in need thereof a composition comprising: a) a fragment of human thrombomodulin in a therapeutically effective amount; and b) a pharmaceutically acceptable carrier; wherein the fragment comprises the amino acids Ala242 to Ser515 of SEQ ID NO: 2.

15 Claims, 12 Drawing Sheets

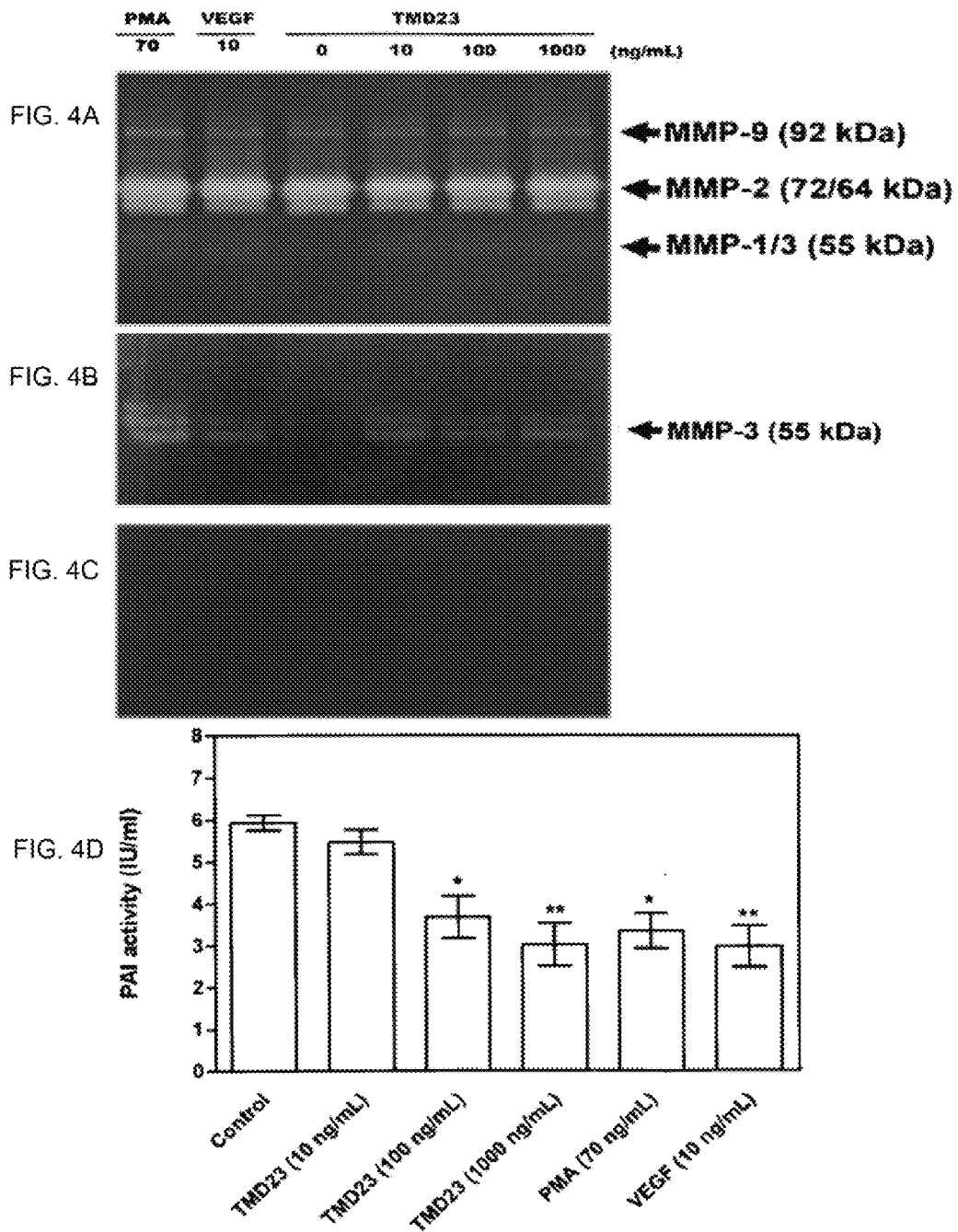

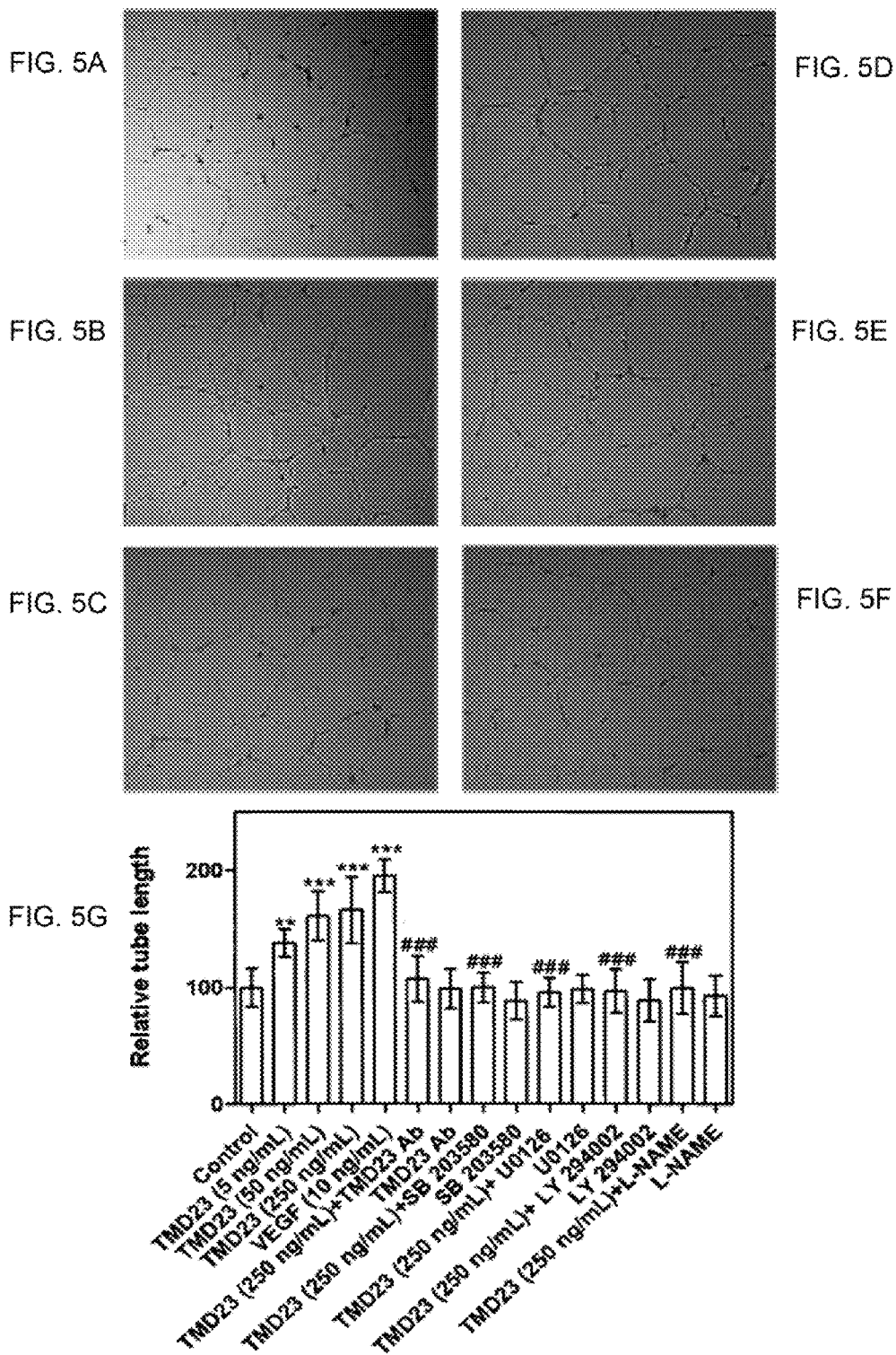

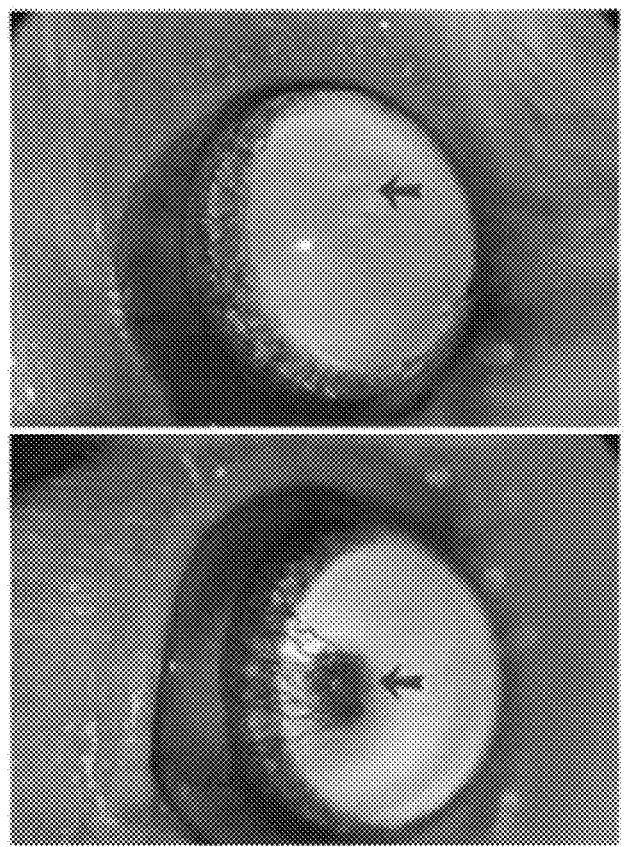
FIG. 6A
FIG. 6B
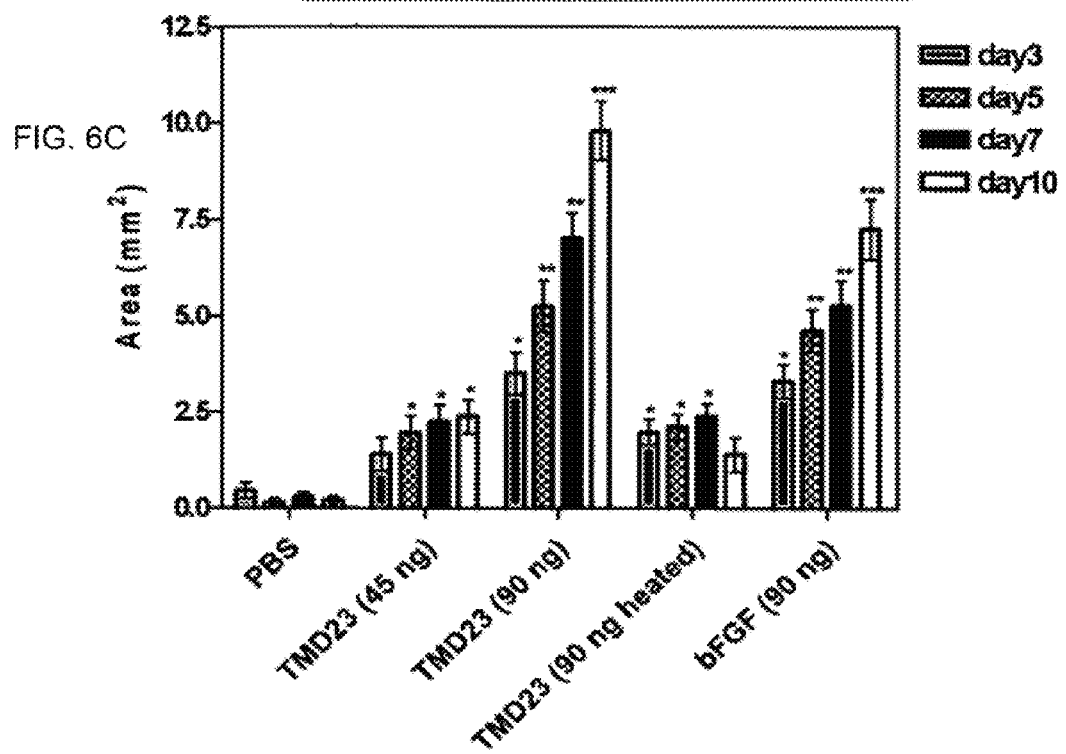
FIG. 6C

METHODS AND COMPOSITIONS FOR TREATING ISCHEMIA

PRIORITY CLAIM

This application is a Divisional of U.S. application Ser. No. 12/316,194 filed Dec. 10, 2008, now U.S. Pat. No. 7,803,367, which is a continuation of U.S. patent application Ser. No. 11/149,378 filed Jun. 9, 2005, which status is abandoned and claims the priority of U.S. Provisional Application Ser. No. 60/641,213 filed on Jan. 3, 2005, all of which are herein incorporated by reference in their entireties.

FIELD OF THE INVENTION

The invention relates to a composition for promoting angiogenesis, for controlling DNA synthesis of a cell, and for controlling chemotactic motility of a cell. The invention also relates to a method for treating ischemia diseases.

BACKGROUND OF INVENTION

Thrombomodulin is an anticoagulant, endothelial-cell-membrane glycoprotein. A recombinant thrombomodulin domain containing six epidermal growth factor-like structures exhibits mitogenic activity.

Although several molecules are known in the art as useful therapeutic agents for the treatment of diseases and disorders having as a symptom thereof abnormal clotting in critical blood vessels, there remains a need in the art for compositions and methods which are useful for the treatment of such diseases as well as for the treatment of diseases and disorders having as symptoms abnormally high or abnormally low muscle cell contractility or undesirable angiogenic activity. Such diseases and conditions include the following: cardiovascular diseases and conditions such as hypotension, hypertension and atherosclerosis; thrombotic conditions such as stroke, heart attack and post angioplasty stenting; angiogenic disorders; respiratory diseases and conditions such as pulmonary fibrosis and asthma; diseases and disorders related to tumor cell invasion, angiogenesis and metastasis; wound healing and clotting disorders and reproductive disorders such as premature uterine contraction and impotence.

In present day, a number of biomolecules, which induce or promote angiogenesis in tissues, have been identified. The most prominent of these are: growth factors such as vascular endothelial growth factor (VEGF), fibroblast growth factor (FGF), epidermal growth factor (EGF), platelet-derived growth factors (PDGFs) and transforming growth factors (TGFs) Healy A M., et al, Absence of the blood-clotting regulator thrombomodulin causes embryonic lethality in mice before development of a functional cardiovascular system. Proc Natl Acad Sci USA. 1995; 92:850-854; and nitric oxide (NO) see, eg, J P Cooke et al, Nitric oxide and angiogenesis. Circulation 105 (2002) 2133-5. The current approaches aimed at promoting angiogenesis in the related field can be summarized into three main categories: (i) delivery of angiogenic growth factors using synthetic and natural polymeric scaffolds; (ii) delivery of plasmids containing DNA that encodes for angiogenic proteins; and (iii) combined delivery of angiogenic molecules and endothelial cell transplantation.

In accordance to the related arts, the invention proposes that loading the delivery systems with human recombinant thrombomodulin molecules instead of growth factors. It is proposed that the loaded human recombinant thrombomodulin can be released under physiological conditions, thus promoting localized, rapid angiogenesis.

TERM DEFINITION

The following definitions are offered for purposes of illustration, not limitation, in order to assist with understanding the discussion that follows.

In accordance with the present invention there may be employed conventional molecular biology, microbiology, and recombinant DNA techniques within persons skilled in the art. Such techniques are explained fully in the literature.

"Angiogenesis"—is generally thought to be heavily regulated by growth factors and other ligands. Angiogenesis, and the concurrent tissue development and regeneration, depends on the tightly controlled processes of endothelial cell proliferation, migration, differentiation and survival. Both stimulator and inhibitor ligands appear to interact, directly or indirectly, with cellular receptors during these processes. Angiogenesis begins with the erosion of the basement membrane by enzymes released by endothelial cells and leukocytes. The endothelial cells, which line the lumen of blood vessels, then protrude through the basement membrane. Angiogenic stimulators induce endothelial cells to migrate through the eroded basement membrane. The migrating cells then form a "sprout" off the parent blood vessel, where the endothelial cells undergo mitosis and proliferate. The endothelial sprouts merge with each other to form capillary loops, creating the new blood vessel.

The term "extracellular matrix" is a complex structure that contains collagen, proteoglycan, glycosaminoglycan, glycoproteins (fibronectin, chondronectin, laminin) and in some tissues, elastin (Hay, E. D., J. Cell Biol., 91: 205-223 (1981)).

The term "Matrix metalloproteinases (MMP's)" is a protein family constitutes the major group of zinc-binding endopeptidases that degrade extracellular matrix proteins, for example connective tissue, collagen and gelatin, during remodeling of connective tissue during normal physiological and some pathological processes. The unrestrained activity of MMP's may result in extensive tissue damage, and these enzymes have been implicated in a variety of disease processes, including tumor cell invasion, tumor angiogenesis and rheumatoid arthritis (Okada, Y., et al., J. Biol. Chem., 261: 14245-14255 (1986)). The MMP's are secreted from cells as inactive zymogens and their activity in the extracellular environment is regulated by various activators and inhibitors (Matrisian, L. M., Trends Genet., 6:121-125 (1990)).

A "nucleic acid" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA molecule that has undergone a molecular biological manipulation.

"Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

As used herein the term "nucleic acid fragment" is intended to indicate any nucleic acid molecule of cDNA, genomic DNA, synthetic DNA or RNA origin. The term "fragment" is intended to indicate a nucleic acid segment which may be single- or double-stranded, and which may be based on a complete or partial naturally occurring nucleotide sequence encoding a polypeptide of interest. The fragment may optionally contain other nucleic acid segments.

The nucleic acid fragment of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction.

An "antisense RNA" refers to a specific sequence of RNA which can be used to inactivate gene expression. An antisense gene codes for an (antisense) RNA that has a complementary sequence to an RNA that is its target. Antisense genes block expression of their targets when introduced into eukaryotic cells. Base pairing offers a powerful means for one RNA to control the activity of another. There are many cases in both prokaryotes and eukaryotes where a (usually rather short) single-stranded RNA base pairs with a complementary region of an mRNA, and as a result prevents expression of the mRNA. One of the early illustrations of this effect was provided by an artificial situation, in which antisense genes were introduced into eukaryotic cells. This technique offered an early approach for turning off genes at will; for example, the function of a regulatory gene can be investigated by introducing an antisense version. Using the same principle, now we have more sophisticated possibilities as the result of the discovery that small RNAs can inhibit expression of complementary sequences.

RNAi is normally triggered by long stretches of double stranded RNA (dsRNA). This is then processed in the cell by an RNase III-like enzyme called Dicer to form short dsRNAs 21-25 nt in length, known as short interfering RNAs (siRNA). When working with mammalian systems, long dsRNA cannot be added to cells without inducing an interferon response, so siRNAs are added instead. This can either be in the form of chemically synthesised siRNA or transcribed from a siRNA expression vector to form a short hairpin RNA (shRNA).

Once processed by Dicer, these siRNAs can enter a multi-enzyme complex known as the RNA-induced silencing complex (RISC). RISC then unwinds the siRNA, incorporating one of the two strands and it is this strand that is then used by RISC to identify a complementary mRNA target. The final result is the degradation of the mRNA target.

Oligonucleotide-mediated antisense and siRNA-mediated RNA interference (RNAi) offer a precise and specific means of knocking down expression of a target gene in any biological system. Gene expression relies on a genomic DNA sequence being transcribed into a messenger RNA (mRNA) that is in turn translated into protein. An antisense or siRNA recognises a specific mRNA target and blocks or degrades it, preventing its translation. Any protein encoded by the target gene thus depletes as a function of its half-life and a rapid and specific knockdown is achieved.

SUMMARY OF THE INVENTION

In one aspect, the invention relates to a method for treating ischemia that would benefit from angiogenesis comprising administering to a subject in need thereof a composition comprising: a) a fragment of human thrombomodulin in a therapeutically effective amount; and (b) a pharmaceutically acceptable carrier; wherein the fragment comprises the amino acids Ala242 to Ser515 of SEQ ID NO: 2.

In another aspect, the invention relates to a method for treating ischemia that would benefit from angiogenesis comprising administering to a subject in need thereof a composition comprising: a) a fragment of human thrombomodulin in a therapeutically effective amount; and b) a pharmaceutically acceptable carrier; wherein the fragment consists of the amino acids Ala242 to Ser515 of SEQ ID NO: 2.

Further in another aspect, the invention relates to method for treating ischemia that would benefit from angiogenesis comprising administering to a subject in need thereof a composition comprising: a) a fragment of human thrombomodulin in a therapeutically effective amount; b) a thrombin; and c) a pharmaceutically acceptable carrier; wherein the fragment consists of the amino acids Ala242 to Ser515 of SEQ ID NO: 2.

Yet in another aspect, the invention relates to a composition comprising: a) a fragment of human thrombomodulin in a therapeutically effective amount; and b) a pharmaceutically acceptable carrier.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 4A shows TMD23 stimulated expression of MMP-1/3; FIG. 4B shows the increased MMP-3 expression was confirmed by caseinolytic zymography; FIG. 4C shows the increased MMP-3 was blocked specifically by EDTA; FIG. 4D shows TMD23 decreased Plasminogen Activator Inhibitor (PAI) Activity in a TMD23-treated HUVEC culture medium.

FIG. 5A shows a control culture developed small amounts of tube formation and incomplete networks within 24 h; FIGS. 5B-5E show HUVECs stimulated with TMD23 formed elongated capillary-like structures, with complete networks by 24 h; FIG. 5F shows the effect of TMD23 on HUVEC tube formation was blocked by anti-TMD23, U0126, SB 203580, LY 294002, and NG-nitro-L-arginine methyl ester (L-NAME, an inhibitor of NO production); FIG. 5G shows the concentration-dependent effect of TMD23 on tube length.

FIG. 6A is a photograph of a control cornea that showed no angiogenic response; FIG. 6B is a photograph of a TMD23-treated cornea that showed neovascularization; FIG. 6C is a graph showing TMD23 induced dose-dependent and time-dependent corneal neovascularization.

DETAILED DESCRIPTION OF THE INVENTION

Figure 1:
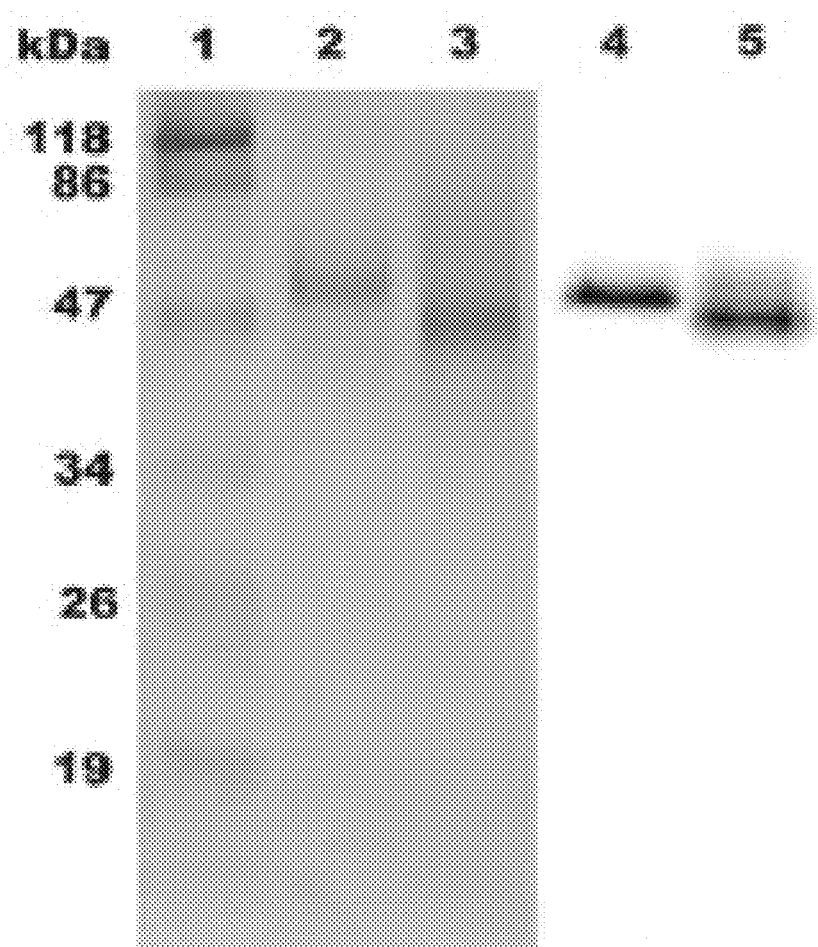
FIG. 1 is expression and purification of TMD2 and TMD23.

Thrombomodulin is an anticoagulant, endothelial-cell-membrane glycoprotein. A recombinant thrombomodulin domain containing six epidermal growth factor-like structures exhibits mitogenic activity. The invention relates to the recombinant domain's novel angiogenic effects using in vitro and in vivo models.

In the present invention, human recombinant thrombomodulin containing six epidermal growth factor-like structures (TMD2) and TMD2 plus a serine and threonine-rich domain (TMD23) were prepared using the *Pichia pastoris* expression system. Combined with purified TMD2 or TMD23, thrombin effectively activated protein C. TMD23 had higher activity than TMD2 in stimulating DNA synthesis in cultured human umbilical vein endothelial cells (HUVECs). Additionally, TMD23 stimulated chemotactic motility and capillary-like tube formation in HUVECs, an effect mediated through phosphorylation of extracellular signal-regulated kinase 1/2 and p38 mitogen-activated protein kinase and the phosphatidylinositol-3 kinase/Akt/endothelial nitric oxide synthase pathway. TMD23 also stimulated endothelial-cell expression of matrix metalloproteinases and plasminogen activators, which mediated extracellular proteolysis leading to endothelial-cell invasion and migration during angiogenesis. Furthermore, TMD23-containing implants in rat cornea induced ingrowth of new blood vessels from the limbus. Using the murine angiogenesis assay, TMD23 not only induced neovascularization coinjected with Matrigel and heparin but also enhanced angiogenesis in Matrigel containing melanoma A2058 cells in nude mice.

The recombinant thrombomodulin domain TMD23 enhanced the angiogenic response in vitro and in vivo, suggesting that thrombomodulin fragments may play a role in formation of new vessels. These findings may provide a new therapeutic option for treating ischemic diseases.

The present invention provides a composition for promoting angiogenesis, comprising a composition including a polypeptide comprising amino acid sequence or a conservative variant thereof having EGF-like domain of thrombomodulin. In the preferred embodiment, the composition of the invention further comprises an operably linked polypeptide comprising amino acid sequence or a conservative variant of serine-threonine rich domain of thrombomodulin. In the preferred embodiment, the promotion of angiogenesis is related to stimulate new capillary formation from endothelial cells. In a more preferred embodiment, the new capillary forms vessel.

The composition of the invention could be used in a cell-based therapy for treating ischemia related diseases. In the preferred embodiment, the endothelial cells express matrix metalloproteinases or plasminogen activators. In the more preferred embodiment, the matrix metalloproteinases or plasminogen activators mediate extracellular proteolysis leading to endothelial-cell invasion and migration during angiogenesis.

In the clinical use, the composition of the invention could help wound healing or reconstructive surgery.

In the present invention, the ischemia related disease is such as myocardial ischemia, peripheral ischemia, cerebral ischemia or deep vein thrombosis.

In the invention, the stimulation of new capillary formation is mediated through phosphorylation of extracellular signal-regulated kinase 1/2 and p38 mitogen-activated protein kinase and phosphatidylinositol-3 kinase/Akt/endothelial nitric oxide synthase pathway.

The composition of the invention further comprises additional carriers or excipients such a gel, cream, paste, lotion, spray, suspension, solution, dispersion salve, hydrogel or ointment formulation.

The present invention also provides a composition for controlling DNA synthesis of a cell, comprising an agent antagonizing specifically to a fragment of polypeptide or nucleotide derived from thrombomodulin. In the preferred embodiment, the polypeptide further comprises an operably linked polypeptide comprising amino acid sequence or a conservative variant of serine-threonine rich domain of thrombomodulin.

In the preferred embodiment, the DNA synthesis is directed to the result of abnormal cell growth. In the more preferred embodiment, the abnormal cell is a result of tumor cell proliferation. In the most preferred embodiment, the tumor is directed to angioma.

The present invention further provides a composition for controlling chemotactic motility of a cell, comprising an agent antagonizing specifically to a fragment of polypeptide or nucleotide derived from thrombomodulin. In the preferred embodiment, the fragment is sufficient to produce an effect of chemotactic motility on a cell. In the more preferred embodiment, the polypeptide further comprises an operably linked polypeptide comprising amino acid sequence or a conservative variant of serine-threonine rich domain of thrombomodulin.

In the further more preferred embodiment, the composition controlling cell chemotactic motility is in the form of antibody, RNAi, siRNA or antisense RNA. In the more preferred embodiment, the chemotactic motility is directed to the result of tumor metastasis. In particular, the chemotactic motility of the cell is mediated through phosphorylation of extracellular signal-regulated kinase 1/2 and p38 mitogen-activated protein kinase and phosphatidylinositol-3 kinase/Akt/endothelial nitric oxide synthase pathway.

The present invention also provides a method for treating ischemia associated with angiogenesis comprising administering to a patient in need of the treatment with a therapeutically effective amount of a polypeptide comprising amino acid sequence or a conservative variant thereof having EGF-like domain of thrombomodulin. In the preferred embodiment, the polypeptide of the composition further comprises an operably linked polypeptide comprising amino acid sequence of serine-threonine rich domain of thrombomodulin.

The administration of the polypeptide is by route of intravenous (iv), subcutaneous (sc), intraperitoneal (ip), or intramuscular (im). In the preferred embodiment, the administration of the polypeptide is by means of gene transfer.

For further understanding of the diseases related to the present invention, by which offering inhibitors or antagonist of angiogenesis via the mechanisms against TMD2 or TMD23 as a therapy is disclosed thereafter. Such diseases and processes, may for example include, but are not limited to, preventing tumor growth, inhibiting tumor growth, reduction in tumor volume, elimination of tumors, inhibiting metastasis, preventing metastasis, inducing dormancy of tumors and metastasis, reducing hemangioma, solid tumors, leukemia, myocardial angiogenesis, neovascular glaucoma, diabetic retinopathy, retrolental fibroplasia, arthritis, diabetic neovascularizaton, macular degeneration, wound healing, peptic ulcer, fractures, keloids, hematopoiesis, ovulation, menstruation, or placentation.

The present invention will be described in detail below.

Material and Processes:

Expression and Purification of Recombinant TMD Proteins

The pPICZaA vector (Invitrogen Corporation) was used for expression and secretion of recombinant human TMD2 and TMD23 in the *Pichia pastoris* protein expression system. Briefly, DNA fragments coding for TMD2 (residues Ala242-Cys480 of SEQ ID NO: 2) and TMD23 (residues Ala242-Ser515 of SEQ ID NO: 2) were obtained by a polymerase chain reaction of human umbilical vein endothelial cell cDNA using primers as described previously. Han H S., et al. Effect of thrombomodulin on plasminogen activation. Fibrinolysis and Proteolysis. 2000; 14: 221-228. Fermentation medium containing expressed TMD2 or TMD23 was applied to a nickel-chelating Sepharose column (Amersham Pharmacia Biotech AB), and TMD-containing fractions were eluted with imidazole.

Thrombomodulin Activity Assay

Cofactor activity of TMD2 and TMD23 for thrombin-dependent protein C activation was measured as described previously. Huang H C., et al Thrombomodulin-mediated cell adhesion: Involvement of its lectin-like domain. J Biol. Chem. 2003; 278:46750-46759.

Cell Proliferation Assay

To evaluate the effect of TMD proteins on DNA synthesis in human umbilical vein endothelial cells (HUVECs), we performed a 5-bromo-2'-deoxyuridine (BrdU) incorporation assay with a commercial quantification kit (Roche Diagnostic GmbH) and manufacturer's protocol. Mitogenic effects induced by TMD proteins were also determined in the presence of polyclonal rabbit anti-TMD23 antibody (prepared by GlycoNex, Inc., Taiwan) that was purified by protein G-Sepharose column (Amersham Pharmacia Biotech AB).

Chemotaxis Assay

The chemotactic motility of HUVECs was assayed using Transwell (Costar) with 6.5-mm diameter polycarbonate filters (8-μm pore size). The lower filter surface was coated with 10 μg gelatin (Sigma-Aldrich). Various concentrations of TMD23 in the absence or presence of 10 μg/mL polyclonal rabbit anti-TMD23 antibody or 10 ng/mL vascular endothelial growth factor (VEGF) (R & D Systems, Inc.) in M199 were placed in the lower wells. One hundred mL cell suspension containing $1\times10^5$ cells was loaded into each of upper well. The chamber was incubated at 37° C. for 4 h. Cells were fixed with methanol and stained with 4',6'-diamidino-2-phenylindole (DAPI). Chemotaxis was quantified with optical microscopy (Leica) at 100× magnification using MetaMorph imaging software (Universal Imaging Corporation) by counting the cells that migrated to the filter's lower side. Five random fields in each well were counted. Each sample was assayed in triplicate, and assays were repeated three times. To determine the role of extracellular signal-regulated kinase 1/2 (ERK1/2), p38 mitogen-activated protein kinase (MAPK), and phosphatidylinositol 3-kinase (PI3 kinase)-protein kinase B/Akt (Akt) in TMD23-mediated cell migration, assays were performed in the presence of U0126, a MAPK/ERK kinase (MEK) inhibitor, SB 203580, a p38 MAPK inhibitor, and LY 294002, a PI3 kinase inhibitor. Cell viability as determined by trypan blue staining was not altered by treatment. 00126 was purchased from Promega, with SB 203580 and LY 294002 from Calbiochem.

Assay of ERK1/2, p38 MAPK, Akt, and Endothelial Nitric Oxide Synthase (eNOS) Phosphorylation HUVECs were cultured to confluence in a 6-cm-diameter dish and incubated in M199 containing 1% FBS for 18 h. Cells were washed and incubated with serum-free M199 for 6 h, and treated with the indicated concentration of TMD23. Cell lysates were separated by SDS-PAGE, and the levels of phospho-ERK1/2 (Tyr 204) and total ERK1/2, phospho-p38 (Thr-180/Tyr-182) and p38, phosphor-Akt (Ser-473) and Akt, and phospho-eNOS (Ser-1173) and eNOS were detected by Western blotting with specific antibodies (Cell Signaling Technology).

Gelatin and Casein Zymographies and Plasminogen Activator Inhibitor (PAI) Activity Assay HUVECs were seeded at 80% confluence on 100-mm dishes in M199 medium. After 24 h, cells were rinsed with serum-free M199 twice and incubated in serum-free M199 with various concentrations of TMD23, VEGF (10 ng/mL), or PMA (70 ng/mL) for 12 h. The conditioned medium containing 5 mg secreted proteins was analyzed by gelatin- and casein-based zymographies. The digested area appeared clear on a blue background, indicating the location of matrix metalloproteinase (MMP) activity. To further verify MMP caseinolytic activity, the casein-containing gel was incubated with incubation buffer containing 10 mM EDTA, an inhibitor of MMPs, to observe disappearance of the clear band. Plasminogen activator inhibitor (PAI) activity was measured by titrating samples with increasing amounts of tissue-type plasminogen activator (t-PA) (Boehringer Ingelheim) into a fixed volume of endothelial-cell-conditioned media.

In Vitro Matrigel Angiogenesis Assay

Growth-factor-reduced Matrigel (BD Biosciences) was thawed at 4° C. A total of 200 μL Matrigel was added to wells of a 48-well plate and polymerized 30 min at 37° C. Two hundred μL cell suspension containing various concentrations of VEGF, TMD23, or TMD23 in the presence of polyclonal rabbit anti-TMD23 antibody (10 μg/mL) or various signaling pathway inhibitors were plated onto Matrigel-coated wells at a density of $2.4\times10^4$ cells/well in M199 containing 10% FBS for 24 h at 37° C. in a 5% $CO_2$ humidified atmosphere. Each concentration was tested in triplicate in the same plate, with wells photographed using a Leica camera (40× magnification). Tube length was quantified by measuring tubes in five randomly chosen fields from each well using MetaMorph software. Experiments were repeated at least three times.

Rat Corneal Angiogenesis Assay

The rat corneal assay was performed as described elsewhere. See eg., Kenyon B M., et al A model of angiogenesis in the mouse cornea. Invest Opthalmol Vis Sci. 1996; 37:1625-1632. Uniformly sized pellets of Hydron (polyhydroxyethylmethacrylate [poly HEMA]) (Sigma-Aldrich) containing either TMD23 or basic fibroblast growth factor (bFGF) and sucralfate (Sigma-Aldrich) were implanted into the rat corneal stroma adjacent to the temporal limbus. Briefly, sterile-saline suspensions containing 5-40 μg TMD23 or bFGF plus 10 mg sucralfate were made and speed vacuumed for 5 min; 12% Hydron in ethanol was added as described. The suspension was deposited onto an autoclaved, sterilized, 15-mm×15-mm nylon mesh. In some preparations, polyclonal anti-TMD23 IgG (10 μg/mL) was included during pellet preparation to specifically inhibit TMD23 activity. The eyes of Sprague Dawley rats (250-300 g) were topically anesthetized and a single pellet was inserted into a surgically created pocket in the corneal stroma. Corneas were examined daily with a dissecting microscope for up to 24 days for capillary growth. Maximal vessel length, clock h, and vascular areas of corneas of all rats were measured with a slit-lamp stereomicroscope.

Murine Angiogenesis Assay

To assess angiogenic effects in vivo, growth-factor-reduced liquid Matrigel (0.5 mL) containing heparin (60 U/mL) and various concentrations of TMD23, bFGF or VEGF was subcutaneously injected into FVB mice near the abdominal midline. Matrigel with PBS plus heparin served as the negative control, with bFGF and VEGF plus heparin as the positive control. Four days after injection, mice were sacrificed and Matrigel plugs were surgically removed. For macroscopic analysis of angiogenesis, hemoglobin content in Matrigel was measured using Drabkin reagent 525 (Sigma-Aldrich). For histological analysis, rat anti-mouse CD31 (PE-CAM-1, platelet endothelial cell adhesion molecule-1) antibody (Pharmingen) was used. The same specimens were used for hematoxylin and eosin (H&E) staining.

Effect of TMD23 on Tumor Neoangiogenesis

To assess TMD23 effects on tumor neoangiogenesis, $1 \times 10^6$ human melanoma A2058 cells (ATCC® CRL-11147) were mixed with Matrigel (0.5 mL) containing heparin (60 U/mL) and various concentrations of TMD23 and subcutaneously injected into athymic nude mice. Matrigel plugs were harvested after 18 days and frozen in liquid nitrogen. Blood vessels were detected by immunohistochemistry using anti-CD31 antibody as described above. Microvessel density (MVD) was calculated by counting six highly vascularized fields in each section (200× magnification; MetaMorph software).

Statistical Analysis

Data are expressed as mean±standard deviation (SD). Statistical significance was analyzed by unpaired Student's t test. Differences between more than two groups was compared by one-way analysis of variance (ANOVA) followed by a Bonferroni's post hoc test, with $P<0.05$ considered statistically significant.

EXAMPLES

Example 1

Expression and Purification of Recombinant TMD Proteins

The pPICZaA vector (Invitrogen Corporation) was used for expression and secretion of recombinant human TMD2 and TMD23 in the *Pichia pastoris* protein expression system. Briefly, DNA fragments coding for TMD2 (residues Ala242-Cys480 of SEQ ID NO: 2) and TMD23 (residues Ala242-Ser515 of SEQ ID NO: 2) were obtained by a polymerase chain reaction of human umbilical vein endothelial cell cDNA using primers as described previously. Han H S., et al Effect of thrombomodulin on plasminogen activation. fibrinolysis and proteolysis. 2000; 14: 221-228. Fermentation medium containing expressed TMD2 or TMD23 was applied to a nickel-chelating Sepharose column (Amersham Pharmacia Biotech AB), and TMD-containing fractions were eluted with imidazole.

Recombinant TMD2 (the amino acids Ala242-Cys480 of SEQ ID NO: 2) containing six EGF-like structures (D2) and TMD23 (the amino acids Ala242-Ser515 of SEQ ID NO: 2) containing D2 and the serine and threonine (Ser/Thr)-rich domain D3 (molecular masses of 47 and 50 kDa, respectively) were prepared with the *Pichia pastoris* expression system. TMD2 or TMD23 purified from fermentation medium was homogeneous as judged by SDS-PAGE and Western blotting with monoclonal anti-TM antibody (FIG. 1). NH2-terminal sequence analysis demonstrated that TMD2 and TMD23 had an expected single sequence starting at the fusion peptide, Glu-Phe, followed by the sequence TM Ala242 of SEQ ID NO: 2. Comparison with the published sequence of human TM revealed a 'T' to 'C' change at nucleotide 1418 and a corresponding amino acid (aa) change at residue 473 (aa 234 in TMD2 and TMD23) from Val to Ala. Cofactor activity of TMD23 for thrombin-dependent protein C activation was 2,650 pmol of APC formed/min/mg TMD23, which was 25% higher than that of TMD2 on an equal molar basis and higher than the value previously reported for recombinant TMD2. Hamada H., et al The epidermal growth factor-like domain of recombinant human thrombomodulin exhibits mitogenic activity for Swiss 3T3 cells. Blood. 1995; 86: 225-233.

Example 2

Thrombomodulin Activity Assay

Cofactor activity of TMD2 and TMD23 for thrombin-dependent protein C activation was measured as described previously. Huang H C., et al Thrombomodulin-mediated cell adhesion: Involvement of its lectin-like domain. J Biol. Chem. 2003; 278: 46750-46759.

Electrophoresis

Sodium dodecyl sulphate polyacrylamide gel electrophoresis (SDS-PAGE) was performed with Laemmli's procedure using a 12.5% separating gel under reduced conditions. Laemmli U K. Cleavage of structural proteins during the assembly of the head of bacteriophage T4. Nature. 1970; 227: 680-685.

Quantification of Recombinant TMD Proteins

TMD protein concentration was determined using the BCA kit (Pierce) with BSA as standard.

Sequence Analysis

Amino-acid sequence determinations were performed automatically by Edman degradation using a Model 477A sequencer (Applied Biosystems).

Cell Cultures

Endothelial cells were isolated from human umbilical cord veins with previously described methods and cells from the second passage were used in all experiments. Shi G Y., et al., Plasmin and the regulation of tissue-type plasminogen activator biosynthesis in human endothelial cells. J. Biol. Chem.

Cell Proliferation Assay

To evaluate the effect of TMD proteins on DNA synthesis in human umbilical vein endothelial cells (HUVECs), a 5-bromo-2'-deoxyuridine (BrdU) incorporation assay were performed with a commercial quantification kit (Roche Diagnostic GmbH) and manufacturer's protocol. Mitogenic effects induced by TMD proteins were also determined in the presence of polyclonal rabbit anti-TMD23 antibody (prepared by GlycoNex, Inc., Taiwan) that was purified by protein G-Sepharose column (Amersham Pharmacia Biotech AB).

Figure 2A:
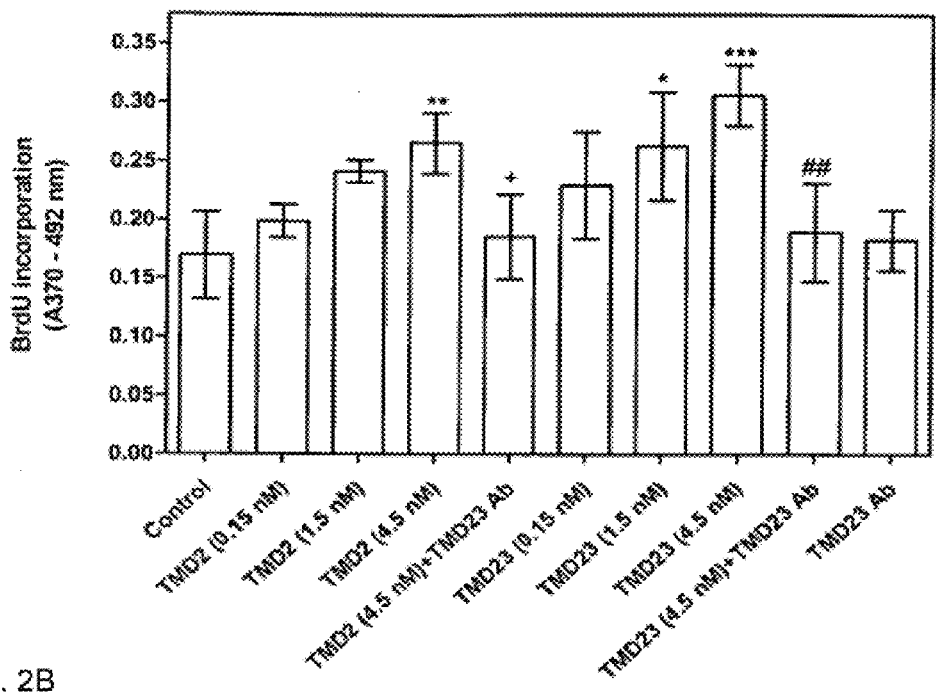
FIG. 2A shows TMD2 and TMD23 induce human umbilical vein endothelial cell (HUVEC) proliferation.

It showed that TMD2 and TMD23 stimulated DNA synthesis in HUVECs and TMD23 had higher mitogenic activity than TMD2 (FIG. 2A). TMD23 at a concentration of 4.5 nM (150 ng/mL) stimulated HUVEC proliferation by roughly two-fold (FIG. 2A). Treatment with polyclonal anti-TMD23 IgG markedly attenuated both TMD2- and TMD23-induced cell proliferation (FIG. 2A) consistent with a TM-specific mitogenic effect.

Chemotaxis Assay

The chemotactic motility of HUVECs was assayed using Transwell (Costar) with 6.5-mm diameter polycarbonate filters (8-μm pore size). The lower filter surface was coated with 10 μg gelatin (Sigma-Aldrich). Various concentrations of TMD23 in the absence or presence of 10 μg/mL polyclonal rabbit anti-TMD23 antibody or 10 ng/mL vascular endothelial growth factor (VEGF) (R & D Systems, Inc.) in M199 were placed in the lower wells. One hundred μL cell suspension containing $1 \times 10^5$ cells was loaded into each of upper well. The chamber was incubated at 37° C. for 4 h. Cells were fixed with methanol and stained with 4',6'-diamidino-2-phenylindole (DAPI). Chemotaxis was quantified with optical microscopy (Leica) at 100× magnification using MetaMorph imaging software (Universal Imaging Corporation) by counting the cells that migrated to the filter's lower side. Five random fields in each well were counted. Each sample was assayed in triplicate, and assays were repeated three times. To determine the role of extracellular signal-regulated kinase 1/2 (ERK1/2), p38 mitogen-activated protein kinase (MAPK), and phosphatidylinositol 3-kinase (PI3 kinase)-protein kinase B/Akt (Akt) in TMD23-mediated cell migration, assays were performed in the presence of U0126, a MAPK/ERK kinase-(MEK) inhibitor, SB 203580, a p38 MAPK inhibitor, and LY 294002, a PI3 kinase inhibitor. Cell viability as determined by trypan blue staining was not altered by treatment. U0126 was purchased from Promega, with SB 203580 and LY 294002 from Calbiochem.

Figure 2B:
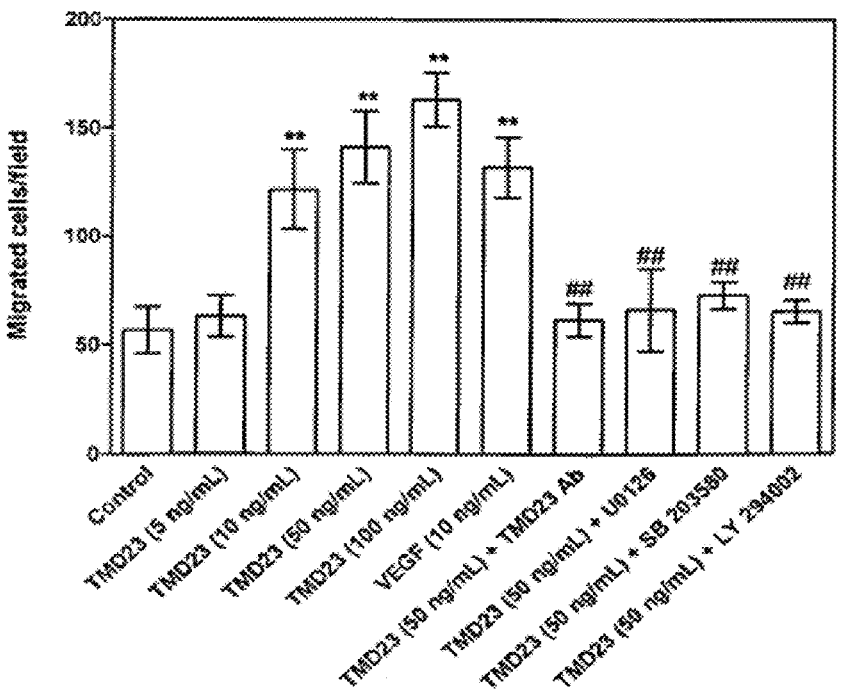
FIG. 2B shows TMD2 and TMD23 induce HUVEC migration.

TMD23 Induces HUVEC Migration. The effect of TMD23 on migration of HUVECs was evaluated using the Transwell assay. As shown in FIG. 2B, TMD23 markedly induced a dose-dependent chemotactic response in HUVECs. The migratory activity at 10 ng/mL TMD23 was increased by 80% over the control, with the effect of TMD23 comparable with that of VEGF (10 ng/mL), a known stimulator of HUVEC migration. The stimulatory effect of TMD23 on HUVEC migration was blocked by U0126, SB 203580, LY 294002, and by a polyclonal antibody against TMD23 (FIG. 2B). This result demonstrated that TMD23 promoted endothelial cell migration may be through ERK1/2, p38, and PI3 kinase/Akt signaling pathways.

Example 3

Assay of ERK1/2, p38 MAPK, Akt, and Endothelial Nitric Oxide Synthase (eNOS) Phosphorylation HUVECs were cultured to confluence in a 6-cm-diameter dish and incubated in M199 containing 1% FBS for 18 h. Cells were washed and incubated with serum-free M199 for 6 h, and treated with the indicated concentration of TMD23. Cell lysates were separated by SDS-PAGE, and the levels of phospho-ERK1/2 (Tyr 204) and total ERK1/2, phospho-p38 (Thr-180/Tyr-182) and p38, phosphor-Akt (Ser-473) and Akt, and phospho-eNOS (Ser-1173) and eNOS were detected by Western blotting with specific antibodies (Cell Signaling Technology).

Figure 3A:
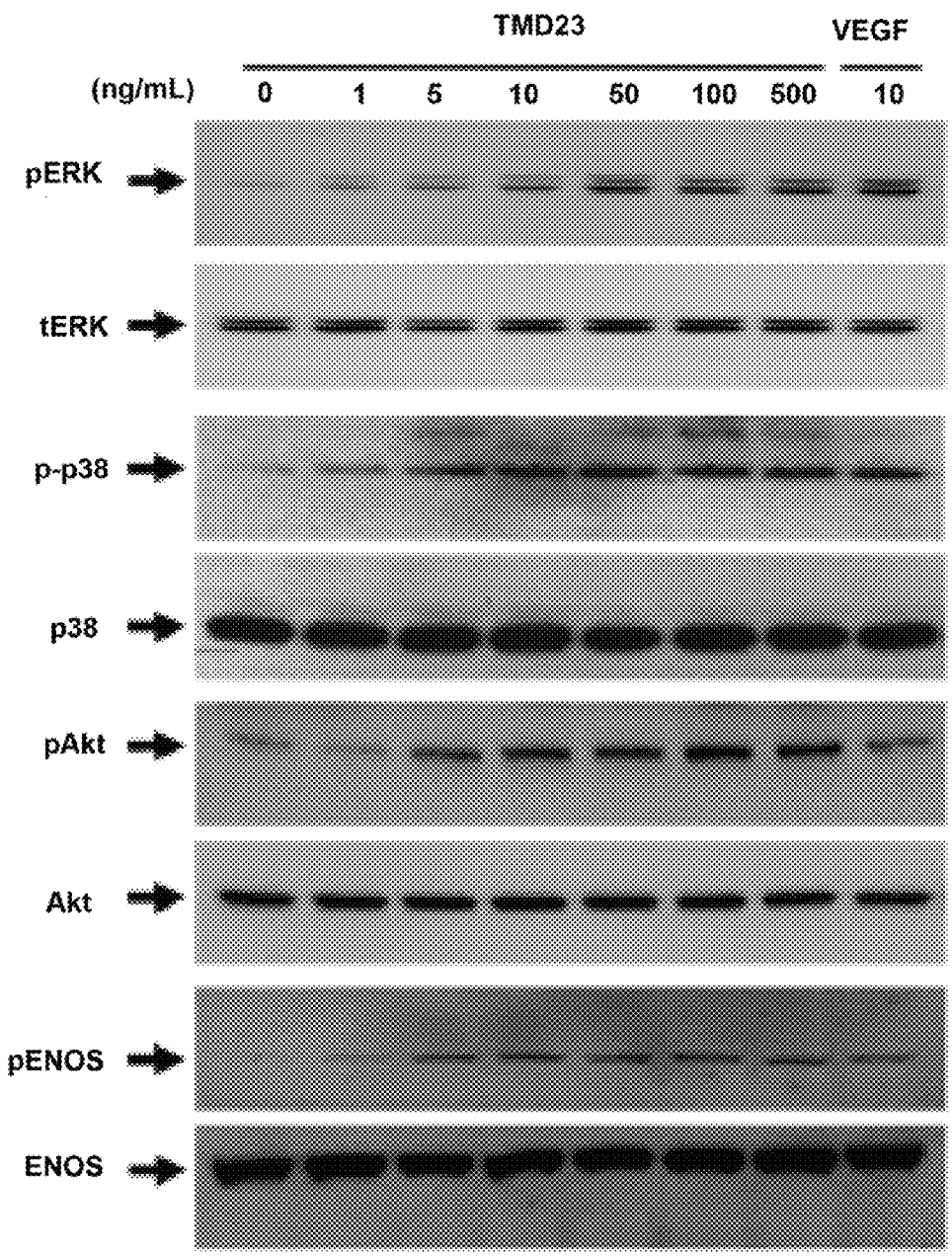
FIG. 3A shows the concentration-dependent effect and FIG. 3B shows the time-dependent effect of TMD23 in inducing activation of ERK1/2, p38 MAPK, Akt, and eNOS in HUVECs.
Figure 3B:
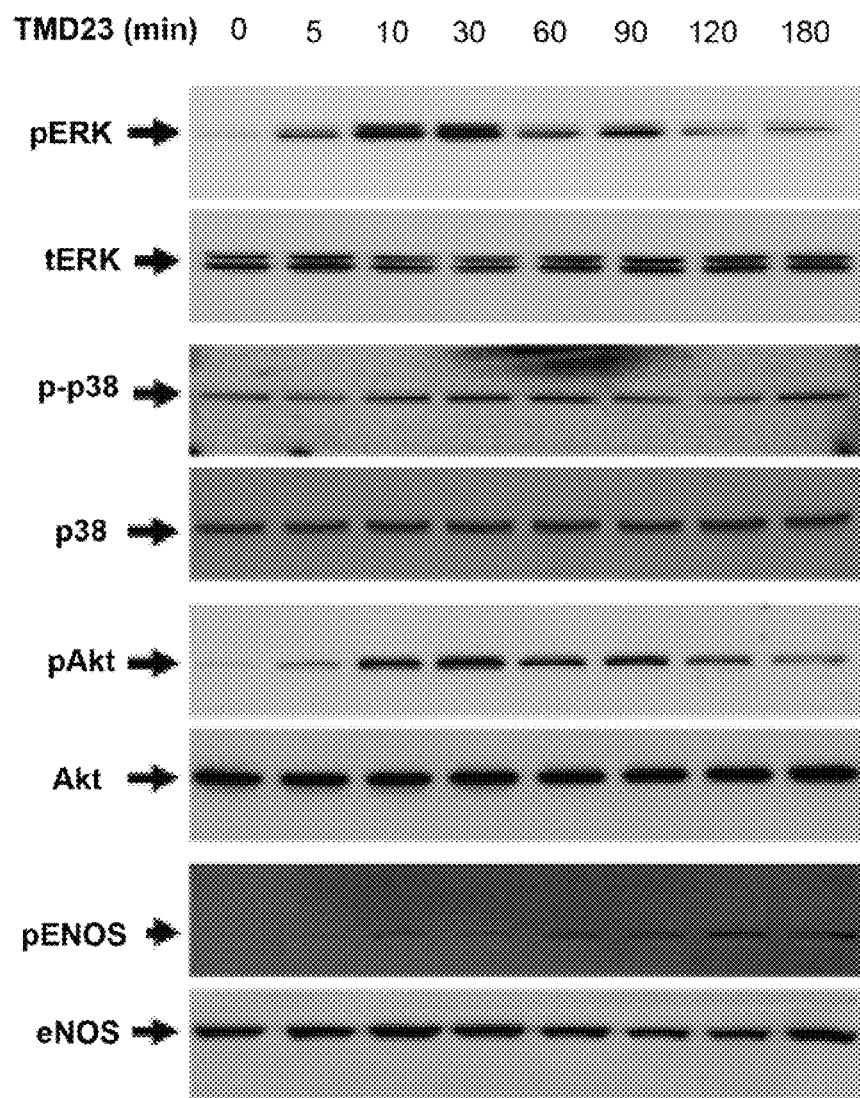

TMD23 Induces ERK1/2, p38 MAPK, Akt, and eNOS Phosphorylation. The ERK pathway, which is activated by many growth factors, may mediate endothelial-cell proliferation and migration. It has also been reported that p38 MAPK activation by VEGF mediates actin reorganization and cell migration in HUVECs, and thus may be an important regulator of angiogenesis. Furthermore, it has been demonstrated that the PI3 kinase/Akt/eNOS signaling axis plays critical roles in angiogenesis. Kawasaki K., et al Activation of the phosphatidylinositol 3-kinase/protein kinase Akt pathway mediates nitric oxide-induced endothelial cell migration and angiogenesis. Mol Cell Biol. 2003; 23: 5726-5737. To validate whether ERK1/2, p38, Akt, and eNOS activity are involved in TM-induced HUVEC proliferation and migration, the effect of TMD23 on ERK1/2, p38, Akt, and eNOS phosphorylation were studied by Western blotting. As shown in FIG. 3A, TMD23 dose-dependently induced ERK1/2, p38, Akt, and eNOS phosphorylation in HUVECs, whereas total ERK, p38, Akt, and eNOS proteins remained constant. Induction of phosphorylation by TMD23 was time-dependent with maximal phosphorylation occurring at about 30 min (ERK, p38, and Akt) and 120 min (eNOS) (FIG. 3B).

Example 4

Gelatin and Casein Zymographies and Plasminogen Activator Inhibitor (PAI) Activity Assay HUVECs were seeded at 80% confluence on 100-mm dishes in M199 medium. After 24 h, cells were rinsed with serum-free M199 twice and incubated in serum-free M199 with various concentrations of TMD23, VEGF (10 ng/mL), or PMA (70 ng/mL) for 12 h. The conditioned medium containing 5 mg secreted proteins was analyzed by gelatin- and casein-based zymographies. Lee O H, et al., Identification of angiogenic properties of insulin-like growth factor II in in vitro angiogenesis models. Brit J. Cancer. 2000; 82:385-391. The digested area appeared clear on a blue background, indicating the location of matrix metalloproteinase (MMP) activity. To further verify MMP caseinolytic activity, the casein-containing gel was incubated with incubation buffer containing 10 mM EDTA, an inhibitor of MMPs, to observe disappearance of the clear band. Plasminogen activator inhibitor (PAI) activity was measured by titrating samples with increasing amounts of tissue-type plasminogen activator (t-PA) (Boehringer Ingelheim) into a fixed volume of endothelial-cell-conditioned media. Shi G Y., et al., Plasmin and the regulation of tissue-type plasminogen activator biosynthesis in human endothelial cells. J Biol. Chem. 1992; 267:19363-19368.

MMPs secreted by various cells including endothelial cells are responsible for degradation of extracellular matrix components, thus facilitating cell migration. Because endothelial-cell migration was stimulated by TMD23. Gelatin and casein zymographies were performed to examine the activities of MMP-1, MMP-2, MMP-3, and MMP-9. TMD23 had no significant effect on expression of MMP-2 and MMP-9, but stimulated expression of MMP-1/3 as shown by gelatin zymography (FIG. 4A). Increased MMP-3 expression was further confirmed by caseinolytic zymography (FIG. 4B), which was blocked specifically in the presence of EDTA (FIG. 4C).

Because MMP and plasminogen activator-plasmin systems play important roles in angiogenesis, we measured the PAI activity of conditioned TMD23-treated cell medium. PAI activity in conditioned media of HUVECs treated with 100 or 1000 ng/mL TMD23, 70 ng/mL PMA, or 10 ng/mL VEGF for 12 h decreased significantly (FIG. 4D), suggesting that both angiogenic factors, TMD23 and VEGF, induced plasminogen activator release into the conditioned media. This result was consistent with the previous observations that VEGF induces urokinase-type plasminogen activator (u-PA) and t-PA in endothelial cells. see eg., Kumar R., et al Regulation of distinct steps of angiogenesis by different angiogenic molecules. Int J. Oncol. 1998; 12:749-757.

Example 5

In Vitro Matrigel Angiogenesis Assay

Growth-factor-reduced Matrigel (BD Biosciences) was thawed at 4° C. A total of 200 µL Matrigel was added to wells of a 48-well plate and polymerized 30 min at 37° C. Two hundred µL cell suspension containing various concentrations of VEGF, TMD23, or TMD23 in the presence of polyclonal rabbit anti-TMD23 antibody (10 µg/mL) or various signaling pathway inhibitors were plated onto Matrigel-coated wells at a density of $2.4 \times 10^4$ cells/well in M199 containing 10% FBS for 24 h at 37° C. in a 5° k $CO_2$ humidified atmosphere. Each concentration was tested in triplicate in the same plate, with wells photographed using a Leica camera (40× magnification). Tube length was quantified by measuring tubes in five randomly chosen fields from each well using MetaMorph software. Experiments were repeated at least three times.

TMD23 Promotes Vascular Tube Formation on Matrigel

Control culture developed small amounts of tube formation and incomplete networks within 24 h (FIG. 5A). However, HUVECs stimulated with VEGF (10 ng/mL) as positive control or TMD23 (5 to 250 ng/mL) formed elongated capillary-like structures, with complete networks observed by 24 h (FIGS. 5B-E). The stimulatory effect of TMD23 on HUVEC tube formation was blocked by polyclonal TMD23 IgG (10 µg/mL), 10 µM U0126, 10 µM SB 203580, 10 µM LY 294002, and 10 µM $N^G$-nitro-L-arginine methyl ester (L-NAME, an inhibitor of NO production) (FIG. 5F). Through counting tubule length per well, TMD23 clearly stimulated tube formation in dose-dependent manner (FIG. 5G). The result of this in vitro assay indicates that TMD23 has a novel vasculogenic or angiogenic activity mediated through ERK1/2, p38, and PI3 kinase/Akt/eNOS signaling pathways.

Example 6

Rat Corneal Angiogenesis Assay

The rat corneal assay was performed as described elsewhere. Uniformly sized pellets of Hydron (polyhydroxyethylmethacrylate [poly HEMA]) (Sigma-Aldrich) containing either TMD23 or basic fibroblast growth factor (bFGF) and sucralfate (Sigma-Aldrich) were implanted into the rat corneal stroma adjacent to the temporal limbus. Briefly, sterile-saline suspensions containing 5-40 µg TMD23 or bFGF plus 10 mg sucralfate were made and speed vacuumed for 5 min; 12% Hydron in ethanol was added as described. The suspension was deposited onto an autoclaved, sterilized, 15-mm× 15-mm nylon mesh. In some preparations, polyclonal anti-TMD23 IgG (10 µg/mL) was included during pellet preparation to specifically inhibit TMD23 activity. The eyes of Sprague Dawley rats (250-300 g) were topically anesthetized and a single pellet was inserted into a surgically created pocket in the corneal stroma. Corneas were examined daily with a dissecting microscope for up to 24 days for capillary growth. Maximal vessel length, clock hour, and vascular areas of corneas of all rats were measured with a slit-lamp stereomicroscope.

TMD23-Induced Angiogenesis in Rat Corneas

Samples were implanted in a vascular rat cornea to allow blood vessel ingrowth from the limbus. Control pellets without growth factors did not induce an angiogenic response (FIGS. 6A, C). Conversely, implants containing TMD23 induced dose-dependent and time-dependent corneal neovascularization (FIGS. 6B, C). Maximal response to TMD23 was observed with a 90-ng dose on day 10, and this was slightly greater than the response to 90 ng bFGF (FIG. 6C). TMD23-induced angiogenic response regressed gradually after day 10 with complete abrogation of response by day 24. To test whether the angiogenic response was dependent on recombinant protein, heat-inactivated TMD23 (100° C. for 30 min) was assayed for angiogenic efficacy. Residual protein C activity of heat-inactivated TMD23 was 40% that of the control without heat treatment, suggesting that the recombinant TMD23 protein was as stable as the natural TM isolated from human placenta or bovine lung. The magnitude of neovascularization response stimulated by 90-ng heated TMD23 sample was about the same as that obtained with 45-ng unheated TMD23 (FIG. 6C). In addition, implants containing 90 ng TMD23 plus polyclonal anti-TMD23 IgG gave no positive responses (n=6), suggesting that the angiogenic response is TMD23-specific.

Example 7

Murine Angiogenesis Assay

To assess angiogenic effects in vivo, growth-factor-reduced liquid Matrigel (0.5 mL) containing heparin (60 U/mL) and various concentrations of TMD23, bFGF or VEGF was subcutaneously injected into FVB mice near the abdominal midline. Matrigel with PBS plus heparin served as the negative control, with bFGF and VEGF plus heparin as the positive control. Four days after injection, mice were sacrificed and Matrigel plugs were surgically removed. For macroscopic analysis of angiogenesis, hemoglobin content in Matrigel was measured using Drabkin reagent 525 (Sigma-Aldrich). For histological analysis, rat anti-mouse CD31 (PE-CAM-1, platelet endothelial cell adhesion molecule-1) antibody (Pharmingen) was used. The same specimens were used for hematoxylin and eosin (H&E) staining.

TMD23 Induces Angiogenesis in the Matrigel Plug Assay In Vivo

Figure 7A:
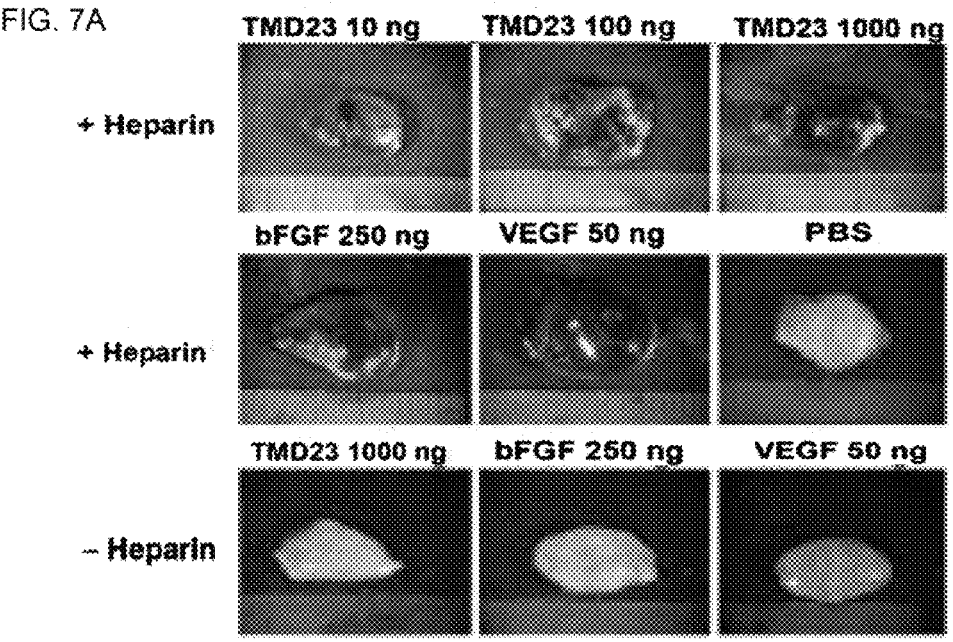
FIG. 7A are micrographs of Matrigel plugs showing heparin-dependent induction of angiogenesis by TMD23.

To further evaluate TMD23 angiogenesis effects in vivo, liquid Matrigel containing various amounts of TMD23 (10, 100, or 1,000 ng), bFGF (250 ng), or VEGF (50 ng) plus heparin (30 U), or heparin alone was injected into FVB mice. FIG. 7A displays the appearances of plugs recovered on day 4. The control plugs were pale, whereas plugs containing TMD23, bFGF, and VEGF plus heparin were bright red (FIG. 7A). Intense vascularization was observed at all TMD23 concentrations and with the positive controls (FIG. 7A). The angiogenic response was apparent in gels 2-3 days after injection, reaching a maximum at 3-5 days. To clarify the heparin effect on angiogenic-factor-induced angiogenesis, Matrigel plugs containing TMD23, bFGF, or VEGF without heparin were assessed. Plugs containing TMD23, bFGF, and VEGF without heparin were pale (FIG. 7A). The observations exemplified by FIG. 7A were consistent with a heparin-dependent enhancement of the angiogenesis induced by TMD23, bFGF, and VEGF.

Figure 7B:
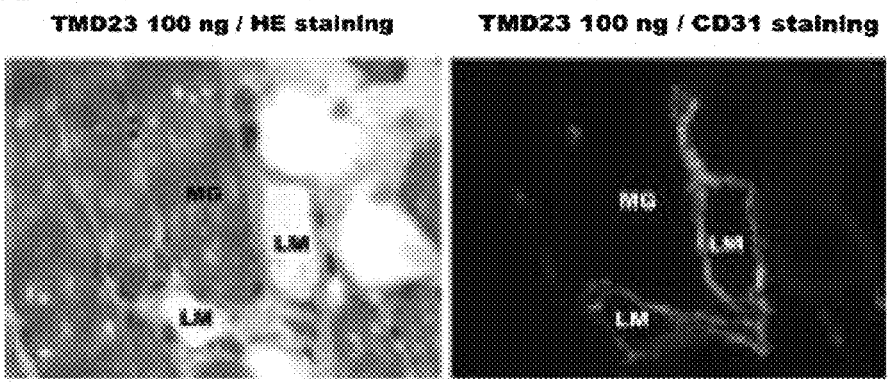
FIG. 7B are micrographs showing capillary-like structures in a hematoxylin-and-eosin (H&E)-stained (left panel) and anti-mouse CD31 (PECAM-1, platelet endothelial cell adhesion molecule-1)-stained sections (right panel) of Matrigel plug containing TMD23 and heparin from an in vivo assay.
Figure 7C:
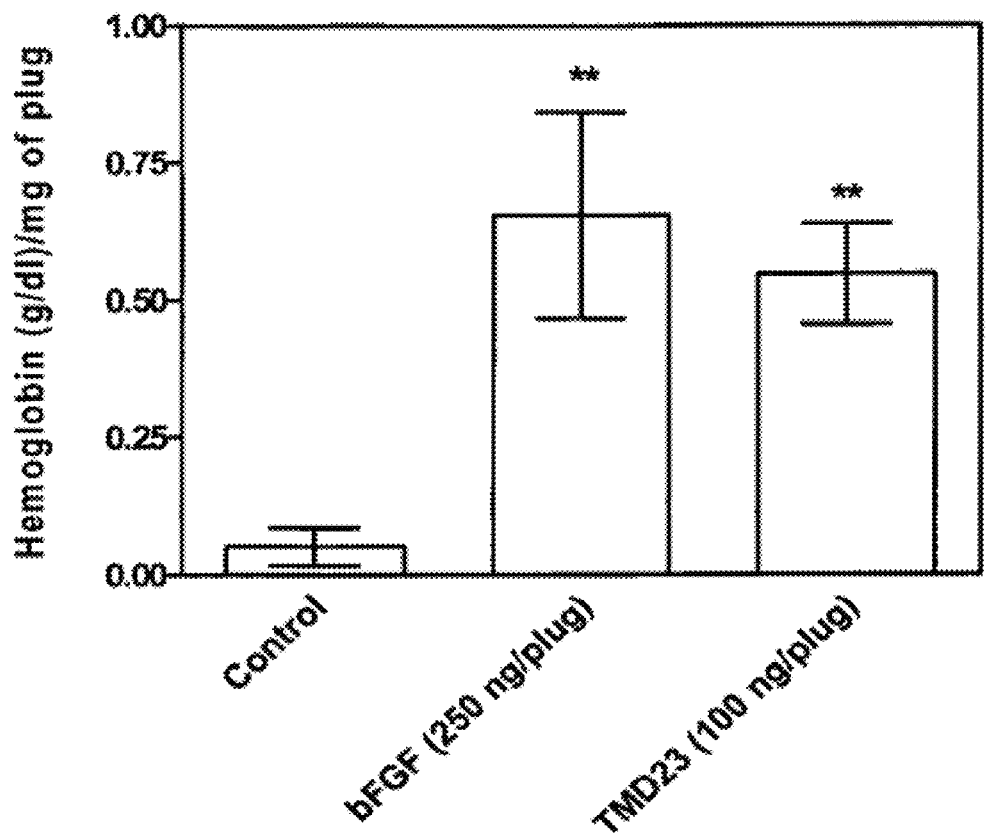
FIG. 7C shows TMD23 plus heparin had significantly increased hemoglobin content compared with controls.

Histological examinations revealed cellular invasion. Capillary-like structures were found in Matrigel plugs with TMD23 and heparin (FIG. 7B). Moreover, use of anti-mouse CD31 (PECAM-1) antibody revealed capillary-like structures had been formed by mouse endothelial cells (FIG. 7B). The latter observation was consistent with the idea that TMD23 could induce endothelial cell invasion and neovessel formation in vivo. The degree of angiogenesis was also determined by measuring the hemoglobin content of recovered Matrigel plugs. Matrigel plugs containing VEGF or TMD23 plus heparin had significantly increased hemoglobin content compared with controls (FIG. 7C).

Example 8

Effect of TMD23 on Tumor Neoangiogenesis

To assess TMD23 effects on tumor neoangiogenesis, $1 \times 10^6$ human melanoma A2058 cells (ATCC® CRL-11147) were mixed with Matrigel (0.5 mL) containing heparin (60 U/mL) and various concentrations of TMD23 and subcutaneously injected into athymic nude mice. Matrigel plugs were harvested after 18 days and frozen in liquid nitrogen. Blood vessels were detected by immunohistochemistry using anti-CD31 antibody as described above. Microvessel density (MVD) was calculated by counting six highly vascularized fields in each section (200× magnification; MetaMorph software).

TMD23 Stimulating Neoangiogenesis in Tumors

Figure 8A:
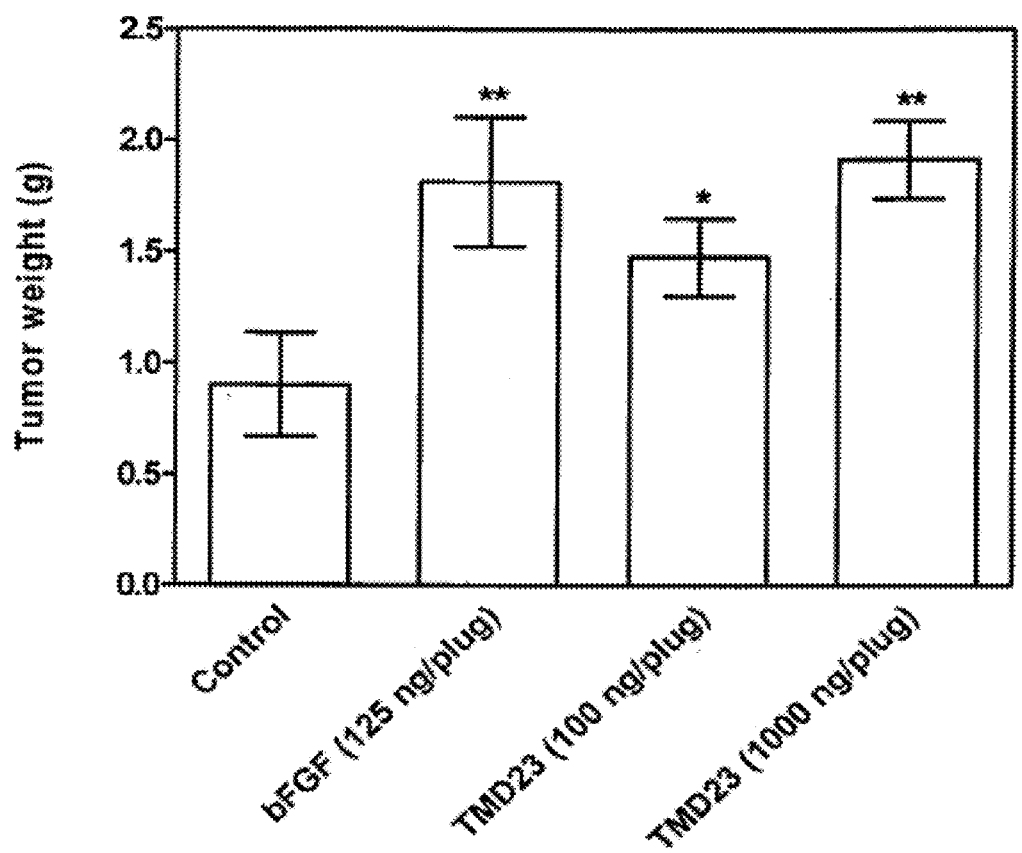
FIG. 8A is a graph showing TMD23 increased the weight of tumor that was contained in a Matrigel plug in vivo.
Figure 8B:
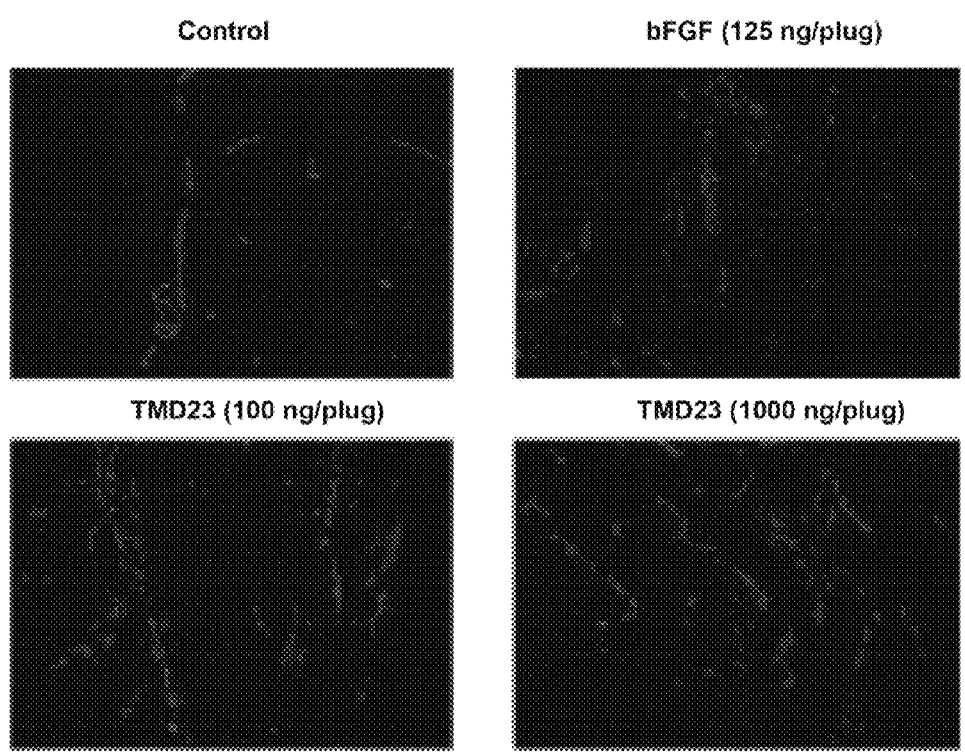
FIG. 8B shows anti-CD31-stained sections of Matrigel plugs, in which Matrigel plugs containing TMD23 induced significantly more blood vessels than the control.
Figure 8C:
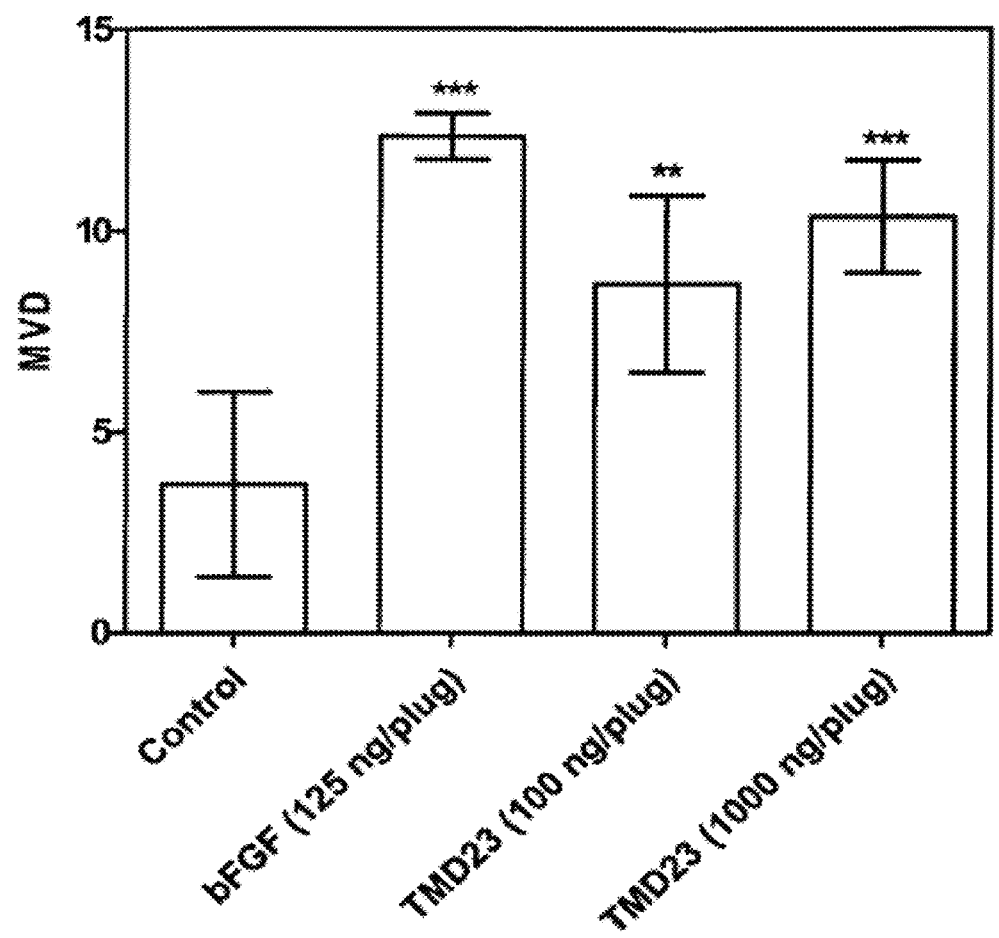
FIG. 8C shows TMD23 increased microvessel density (MVD).

Angiogenesis is an essential step for many physiological and pathological processes, TMD23 effects on tumor neoangiogenesis were assessed. A2058 cells were mixed in Matrigel supplemented with TMD23 and heparin and injected subcutaneously into athymic nude mice. The tumor size developed by Matrigel plugs containing A2058 cells and TMD23 (or bFGF) was bigger than that for A2058 cells alone (FIG. 8A). Immunohistochemical staining of CD31 demonstrated significantly more blood vessels in Matrigel plugs containing TMD23 (or bFGF) (FIGS. 8B, 8C).

Example 9

Results

Neovascularization encompasses both angiogenesis and vasculogenesis. Vasculogenesis is defined as creation of blood vessels by differentiation of endothelial precursor cells (EPCs), whereas angiogenesis represents formation of new capillaries from pre-existing mature endothelial cells, a process including migration and proliferation of endothelial cells, extracellular matrix degradation, and capillary tube formation. Many molecules have been identified that induce vessel formation both in vitro and in vivo including acidic FGF, bFGF, transforming growth factor (TGF)-α, TGF-β, hepatocyte growth factor (HGF), tumor necrosis factor-a, angiogenin, interleukin-8, and angiopoietins. Conversely, thrombospondin, platelet factor-4, angiostatin, arresten, restin, endostatin, and tumstatin have been identified as important endogenous anti-angiogenic molecules. Protease cleavage of collagen types IV, XV, and XVIII generates arresten (and tumstatin), restin, and endostatin, respectively, while plasminogen proteolysis yields angiostatin. Several other molecules and their proteolytic cleavage products have the potential to exert opposing effects on angiogenesis. For example, certain parental proteins including prolactin, growth hormone, and placental lactogen can promote angiogenesis. However, after proteolytic processing the same proteins generate peptide fragments that have anti-angiogenic properties. Corbacho A M., et al., Roles of prolactin and related members of the prolactin/growth hormone/placental lactogen family in angiogenesis. J. Endocrin. 2002; 173: 219-238. The present invention provides a novel angiogenic-promoting function of TM domains 2 and 3. Recombinant TM fragment TMD23 can stimulate endothelial migration, proliferation, and tube formation in vitro, a process that may be mediated via phosphorylation of ERK1/2, p38, Akt, and eNOS. It has been found that TMD23 stimulates endothelial-cell expression of MMPs and plasminogen activators that mediate extracellular proteolysis, leading to endothelial-cell invasion and migration during the early stages of angiogenesis. Using a murine Matrigel model and rat corneal neovascularization assays, it has been found that a TMD23-dependent induction of angiogenesis in vivo. It suggests that TMD23 could become a novel therapeutic agent for some ischemia-related diseases.

The D3 of TM is rich in Ser and Thr, which can support post-translational attachment of a chondroitin sulfate moiety. Bourin M C., et al., Isolation and characterization of the glycosaminoglycan component of rabbit thrombomodulin proteoglycan. J Biol. Chem. 1990; 265: 15424-15431. The present invention demonstrates that TMD23 was more effective than TMD2 in stimulating proliferation of HUVECs (FIG. 2A) and in inducing in vivo angiogenesis using the Matrigel plug assay. These results are in line with previous observations that a novel chondroitin sulfate/dermatan sulfate proteoglycan promotes hepatocyte growth factor mitogenic activity and that a chondroitin sulfate containing glycosaminoglycan enhances in vitro FGF-2-dependent angiogenesis. Tapon-Bretaudiere J et al., A fucosylated Chondroitin sulfate from echinoderm modulats in vitro fibroblast growth factor 2-dependent angiogenesis. Mol Cancer Res. 2002; 1: 96-102.

During the course of the murine angiogenesis assays, it has been found that Matrigel supplemented with either TMD23, bFGF, or VEGF produced a variable angiogenic reaction, but that the magnitude of the reaction was considerably greater in gels that were supplemented with both angiogenic factors and heparin. These results are consistent with previous findings. Matrigel, a solution of basement membrane proteins isolated from the Engelbreth-Holm-Swarm tumor, can serve as a vehicle for slow release of angiogenic factors, with heparin promoting the binding, modulation, and sustained release of these factors. Passaniti A., et al., A simple quantitative method for assessing angiogenesis and antiangiogenic agents using reconstituted basement membrane, heparin, and fibroblast growth factor. Lab Invest. 1992; 67: 519-528. However, heparin is not necessary to obtain the angiogenic response in the rat corneal neovascularization assay because the combination of angiogenic factors with sucralfate and incorporation into Hydron achieves stabilization of angiogenic factors and sustains release over a prolonged time. Kenyon B M., et al., A model of angiogenesis in the mouse cornea. Invest Opthalmol Vis Sci. 1996; 37: 1625-1632.

It has been demonstrated that cell surface proteoglycan syndecan-4 participates in mediating the effects of FGF-2 on cell function. It suggests that the biological activities of TM domains could be mediated by binding of the peptide to its specific site on the cell surface. However, TM domains interact with other membrane molecules such as syndecan or synectin which can mediate or trigger the effects of TM on cell function, as in the case of FGF-2. Therefore, it is possible that TM domains act indirectly.

Expression of TM proteins has been documented in a myriad of tumors and cell lines. An inverse relationship of TM expression and rate of tumor-cell proliferation has been reported in hepatocellular carcinoma, ovarian carcinoma, and esophageal squamous carcinoma. It suggests that various soluble TM fragments released from the cell surface by in situ proteolytic enzymes including plasminogen activators-plasmin, elastase, and MMPs may function as paracrine substances to modulate angiogenesis in tumors. Soluble forms of TM derived from the molecule's extracellular domain have been found in the plasma and urine of healthy subjects, suggesting that it is cleaved under physiological conditions. The increase of plasma TM fragments in patients with various diseases suggests that TM release from endothelial cells is accelerated by proteolytic activity generated on the surface of the endothelium. The proteases responsible for TM shedding are still unknown, although neutrophil-derived enzymes including elastase, proteinase-3, and cathepsin G have been implicated.

In the present invention, it demonstrated the TMD23 can promote angiogenesis in vitro and in vivo. In the in vitro Matrigel assay, TMD23 could promote the morphological differentiation of HUVECs to form tube-like structures with well-connected network. Therefore, TMD23 could induce vasculogenesis.

What is claimed is:

1. A method for treating ischemia comprising administering to a subject in need thereof a composition comprising:
    (a) a fragment of recombinant human thrombomodulin in a therapeutically effective amount;
    (b) an effective amount of thrombin; and
    (c) a pharmaceutically acceptable carrier;
    wherein the fragment of recombinant human thrombomodulin comprises the amino acids Ala242 to Ser515 of SEQ ID NO: 2.

2. The method of claim 1, wherein the ischemia is selected from the group consisting of myocardial ischemia, peripheral ischemia, cerebral ischemia, retina ischemia, and deep vein thrombosis-induced ischemia.

3. The method of claim 2, wherein the composition is in an injectable form.

4. A method for treating ischemia comprising administering to a subject in need thereof a composition comprising:
    (a) a fragment of recombinant human thrombomodulin in a therapeutically effective amount; and
    (b) a pharmaceutically acceptable carrier;
    wherein the fragment of recombinant human thrombomodulin comprises the amino acids Ala242 to Ser515 of SEQ ID NO: 2,
    and the ischemia is selected from the group consisting of peripheral ischemia, cerebral ischemia, retina ischemia, and deep vein thrombosis-induced ischemia.

5. The method of claim 4, wherein the ischemia is cerebral ischemia, retina ischemia, or deep vein thrombosis-induced ischemia.

6. The method of claim 4, wherein the subject is in need of treatment of cerebral ischemia.

7. The method of claim 4, wherein the subject is in need of treatment of peripheral ischemia.

8. A method for treating ischemia comprising administering to a subject in need thereof a composition comprising:
    (a) a fragment of recombinant human thrombomodulin in a therapeutically effective amount; and
    (b) a pharmaceutically acceptable carrier;
    wherein the fragment of recombinant human thrombomodulin consists of the amino acids Ala242 to Ser515 of SEQ ID NO: 2.

9. The method of claim 8, wherein the ischemia is selected from the group consisting of myocardial ischemia, peripheral ischemia, cerebral ischemia, retina ischemia, and deep vein thrombosis-induced ischemia.

10. The method of claim 8, wherein the administering step is replaced by the step of administering to a subject in need thereof a composition comprising:
    (a) a fragment of recombinant human thrombomodulin in a therapeutically effective amount;
    (b) thrombin in a therapeutically effective amount; and
    (c) a pharmaceutically acceptable carrier;
    wherein the fragment of recombinant human thrombomodulin consists of the amino acids Ala242 to Ser515 of SEQ ID NO: 2.

11. The method of claim 10, wherein the ischemia is selected from the group consisting of myocardial ischemia, peripheral ischemia, cerebral ischemia, retina ischemia, and deep vein thrombosis-induced ischemia.

12. The method of claim 10, wherein the subject is in need of treatment of myocardial ischemia.

13. The method of claim 10, wherein the subject is in need of treatment of peripheral ischemia.

14. The method of claim 1, wherein the subject is in need of treatment of myocardial ischemia.

15. The method of claim 1, wherein the subject is in need of treatment of peripheral ischemia.

* * * * *

SEQUENCE LISTING

```
<160> NUMBER OF SEQ ID NOS: 2

<210> SEQ ID NO 1
<211> LENGTH: 4593
<212> TYPE: DNA
<213> ORGANISM: Homo sapiens
<220> FEATURE:
<221> NAME/KEY: CDS
<222> LOCATION: (719)..(2443)

<400> SEQUENCE: 1
ggatccagct gtctctcctt gcgatcctgt cttcggggaa gtccacgtcc taggcaggtc      60
ctcccaaagt gcccttggtg ccgatcaccc ctcccagcgt cttgcaggtc ctgtgcacca     120
cctcccccac tccccattca aagccctctt ctctgaagtc tccggttccc agagctcttg     180
caatccaggc tttccttgga agtggctgta acatgtatga aaagaaagaa aggaggacca     240
agagatgaaa gagggctgca cgcgtggggg cccgagtggt gggcggggac agtcgtcttg     300
ttacaggggt gctggccttc cctggcgcct gccccgtcg gccccgcccg agaacctccc     360
tgcgccaggg cagggtttac tcatcccggc gaggtgatcc catgcgcgag ggcgggcgca     420
agggcggcca gagaacccag caatccgagt atgcggcatc agcccttccc accaggcact     480
tccttccttt tcccgaacgt ccagggaggg agggccgggc acttataaac tcgagccctg     540
gccgatccgc atgtcagagg ctgcctcgca ggggctgcgc gcagcggcaa gaagtgtctg     600
ggctgggacg gacaggagag gctgtcgcca tcggcgtcct gtgcccctct gctccggcac     660
ggccctgtcg cagtgcccgc gctttccccg gcgcctgcac gcggcgcgcc tgggtaac      718 atg ctt ggg gtc ctg gtc ctt ggc gcg ctg gcc ctg gcc ggc ctg ggg      766
Met Leu Gly Val Leu Val Leu Gly Ala Leu Ala Leu Ala Gly Leu Gly
1               5                   10                  15 ttc ccc gca ccc gca gag ccg cag ccg ggt ggc agc cag tgc gtc gag      814
Phe Pro Ala Pro Ala Glu Pro Gln Pro Gly Gly Ser Gln Cys Val Glu
            20                  25                  30 cac gac tgc ttc gcg ctc tac ccg ggc ccc gcg acc ttc ctc aat gcc      862
His Asp Cys Phe Ala Leu Tyr Pro Gly Pro Ala Thr Phe Leu Asn Ala
        35                  40                  45 agt cag atc tgc gac gga ctg cgg ggc cac cta atg aca gtg cgc tcc      910
Ser Gln Ile Cys Asp Gly Leu Arg Gly His Leu Met Thr Val Arg Ser
```

-continued

```
            50                      55                      60
tcg gtg gct gcc gat gtc att tcc ttg cta ctg aac ggc gac ggc ggc    958
Ser Val Ala Ala Asp Val Ile Ser Leu Leu Leu Asn Gly Asp Gly Gly
65                  70                      75                  80 gtt ggc cgc cgg cgc ctc tgg atc ggc ctg cag ctg cca ccc ggc tgc   1006
Val Gly Arg Arg Arg Leu Trp Ile Gly Leu Gln Leu Pro Pro Gly Cys
                    85                      90                  95 ggc gac ccc aag cgc ctc ggg ccc ctg cgc ggc ttc cag tgg gtt acg   1054
Gly Asp Pro Lys Arg Leu Gly Pro Leu Arg Gly Phe Gln Trp Val Thr
            100                     105                     110 gga gac aac aac acc agc tat agc agg tgg gca cgg ctc gac ctc aat   1102
Gly Asp Asn Asn Thr Ser Tyr Ser Arg Trp Ala Arg Leu Asp Leu Asn
                115                     120                     125 ggg gct ccc ctc tgc ggc ccg ttg tgc gtc gct gtc tcc gct gct gag   1150
Gly Ala Pro Leu Cys Gly Pro Leu Cys Val Ala Val Ser Ala Ala Glu
130                     135                     140 gcc act gtg ccc agc gag ccg atc tgg gag gag cag cag tgc gaa gtg   1198
Ala Thr Val Pro Ser Glu Pro Ile Trp Glu Glu Gln Gln Cys Glu Val
145                     150                     155                 160 aag gcc gat ggc ttc ctc tgc gag ttc cac ttc cca gcc acc tgc agg   1246
Lys Ala Asp Gly Phe Leu Cys Glu Phe His Phe Pro Ala Thr Cys Arg
                    165                     170                 175 cca ctg gct gtg gag ccc ggc gcc gcg gct gcc gcc gtc tcg atc acc   1294
Pro Leu Ala Val Glu Pro Gly Ala Ala Ala Ala Ala Val Ser Ile Thr
            180                     185                     190 tac ggc acc ccg ttc gcg gcc cgc gga gcg gac ttc cag gcg ctg ccg   1342
Tyr Gly Thr Pro Phe Ala Ala Arg Gly Ala Asp Phe Gln Ala Leu Pro
                195                     200                     205 gtg ggc agc tcc gcc gcg gtg gct ccc ctc ggc tta cag cta atg tgc   1390
Val Gly Ser Ser Ala Ala Val Ala Pro Leu Gly Leu Gln Leu Met Cys
210                     215                     220 acc gcg ccg ccc gga gcg gtc cag ggg cac tgg gcc agg gag gcg ccg   1438
Thr Ala Pro Pro Gly Ala Val Gln Gly His Trp Ala Arg Glu Ala Pro
225                     230                     235                 240 ggc gct tgg gac tgc agc gtg gag aac ggc ggc tgc gag cac gcg tgc   1486
Gly Ala Trp Asp Cys Ser Val Glu Asn Gly Gly Cys Glu His Ala Cys
                    245                     250                 255 aat gcg atc cct ggg gct ccc cgc tgc cag tgc cca gcc ggc gcc gcc   1534
Asn Ala Ile Pro Gly Ala Pro Arg Cys Gln Cys Pro Ala Gly Ala Ala
                260                     265                     270 ctg cag gca gac ggg cgc tcc tgc acc gca tcc gcg acg cag tcc tgc   1582
Leu Gln Ala Asp Gly Arg Ser Cys Thr Ala Ser Ala Thr Gln Ser Cys
                    275                     280                     285 aac gac ctc tgc gag cac ttc tgc gtt ccc aac ccc gac cag ccg ggc   1630
Asn Asp Leu Cys Glu His Phe Cys Val Pro Asn Pro Asp Gln Pro Gly
            290                     295                     300 tcc tac tcg tgc atg tgc gag acc ggc tac cgg ctg gcg gcc gac caa   1678
Ser Tyr Ser Cys Met Cys Glu Thr Gly Tyr Arg Leu Ala Ala Asp Gln
305                     310                     315                 320 cac cgg tgc gag gac gtg gat gac tgc ata ctg gag ccc agt ccg tgt   1726
His Arg Cys Glu Asp Val Asp Asp Cys Ile Leu Glu Pro Ser Pro Cys
                    325                     330                 335 ccg cag cgc tgt gtc aac aca cag ggt ggc ttc gag tgc cac tgc tac   1774
Pro Gln Arg Cys Val Asn Thr Gln Gly Gly Phe Glu Cys His Cys Tyr
                340                     345                     350 cct aac tac gac ctg gtg gac ggc gag tgt gtg gag ccc gtg gac ccg   1822
Pro Asn Tyr Asp Leu Val Asp Gly Glu Cys Val Glu Pro Val Asp Pro
                355                     360                     365 tgc ttc aga gcc aac tgc gag tac cag tgc cag ccc ctg aac caa act   1870
Cys Phe Arg Ala Asn Cys Glu Tyr Gln Cys Gln Pro Leu Asn Gln Thr
```

-continued

```
         370                375                380
agc tac ctc tgc gtc tgc gcc gag ggc ttc gcg ccc att ccc cac gag    1918
Ser Tyr Leu Cys Val Cys Ala Glu Gly Phe Ala Pro Ile Pro His Glu
385                 390                 395                 400 ccg cac agg tgc cag atg ttt tgc aac cag act gcc tgt cca gcc gac    1966
Pro His Arg Cys Gln Met Phe Cys Asn Gln Thr Ala Cys Pro Ala Asp
                405                 410                 415 tgc gac ccc aac acc cag gct agc tgt gag tgc cct gaa ggc tac atc    2014
Cys Asp Pro Asn Thr Gln Ala Ser Cys Glu Cys Pro Glu Gly Tyr Ile
            420                 425                 430 ctg gac gac ggt ttc atc tgc acg gac atc gac gag tgc gaa aac ggc    2062
Leu Asp Asp Gly Phe Ile Cys Thr Asp Ile Asp Glu Cys Glu Asn Gly
        435                 440                 445 ggc ttc tgc tcc ggg gtg tgc cac aac ctc ccc ggt acc ttc gag tgc    2110
Gly Phe Cys Ser Gly Val Cys His Asn Leu Pro Gly Thr Phe Glu Cys
450                 455                 460 atc tgc ggg ccc gac tcg gcc ctt gtc cgc cac att ggc acc gac tgt    2158
Ile Cys Gly Pro Asp Ser Ala Leu Val Arg His Ile Gly Thr Asp Cys
465                 470                 475                 480 gac tcc ggc aag gtg gac ggt ggc gac agc ggc tct ggc gag ccc ccg    2206
Asp Ser Gly Lys Val Asp Gly Gly Asp Ser Gly Ser Gly Glu Pro Pro
                485                 490                 495 ccc agc ccg acg ccc ggc tcc acc ttg act cct ccg gcc gtg ggg ctc    2254
Pro Ser Pro Thr Pro Gly Ser Thr Leu Thr Pro Pro Ala Val Gly Leu
            500                 505                 510 gtg cat tcg ggc ttg ctc ata ggc atc tcc atc gcg agc ctg tgc ctg    2302
Val His Ser Gly Leu Leu Ile Gly Ile Ser Ile Ala Ser Leu Cys Leu
        515                 520                 525 gtg gtg gcg ctt ttg gcg ctc ctc tgc cac ctg cgc aag aag cag ggc    2350
Val Val Ala Leu Leu Ala Leu Leu Cys His Leu Arg Lys Lys Gln Gly
530                 535                 540 gcc gcc agg gcc aag atg gag tac aag tgc gcg gcc cct tcc aag gag    2398
Ala Ala Arg Ala Lys Met Glu Tyr Lys Cys Ala Ala Pro Ser Lys Glu
545                 550                 555                 560 gta gtg ctg cag cac gtg cgg acc gag cgg acg ccg cag aga ctc        2443
Val Val Leu Gln His Val Arg Thr Glu Arg Thr Pro Gln Arg Leu
                565                 570                 575 tgagcggcct ccgtccagga gcctggctcc gtccaggagc ctgtgcctcc tcaccccag    2503
ctttgctacc aaagcacctt agctggcatt acagctggag aagaccctcc ccgcacccc    2563
caagctgttt tcttctattc catggctaac tggcgagggg gtgattagag ggaggagaat   2623
gagcctcggc ctcttccgtg acgtcactgg accactgggc aatgatgcca attttgtaac   2683
gaagacacag actgcgattt gtcccaggtc tcactaccg ggcgcaggag ggtgagcgtt    2743
attggtcggc agccttctgg gcagaccttg acctcgtggg ctagggatga ctaaaatatt   2803
tatttttttt aagtatttag gttttgttt gtttcctttg ttcttacctg tatgtctcca    2863
gtatccactt tgcacagctc tccggtctct ctctctctac aaactcccac ttgtcatgtg   2923
acaggtaaac tatcttggtg aattttttt tcctagccct ctcacattta tgaagcaagc    2983
cccactatt ccccattctt cctagttttc tcctcccagg aactgggcca actcacctga    3043
gtcaccctac ctgtgcctga ccctacttct tttgctctta gctgtctgct cagacagaac   3103
ccctacatga aacagaaaca aaaacactaa aaataaaaat ggccatttgc tttttcacca   3163
gatttgctaa tttatcctga aatttcagat tcccagagca aaataatttt aaacaaaggt   3223
tgagatgtaa aaggtattaa attgatgttg ctggactgtc atagaaatta cacccaaaga   3283
ggtatttatc tttactttta aacagtgagc ctgaattttg ttgctgtttt gatttgtact   3343
```

```
gaaaaatggt aattgttgct aatcttctta tgcaatttcc ttttttgtta ttattactta      3403 ttttttgacag tgttgaaaat gttcagaagg ttgctctaga ttgcgagaag agacaaacac     3463
ctcccaggag acagttcaag aaagcttcaa actgcatgat tcatgccaat tagcaattga     3523
ctgtcactgt tccttgtcac tggtagacca aaataaaacc agctctactg gtcttgtgga     3583
attgggagct tgggaatgga tcctggagga tgcccaatta gggcctagcc ttaatcaggt     3643
cctcagagaa tttctaccat ttcagagagg ccttttggaa tgtggcccct gaacaagaat     3703
tggaagctgc cctgcccatg ggagctggtt agaaatgcag aatcctaggc tccaccccat     3763
ccagttcatg agaatctata tttaacaaga tctgcagggg gtgtgtctgc tcagtaattt     3823
gaggacaacc attccagact gcttccaatt ttctggaata catgaaatat agatcagtta     3883
taagtagcag gccaagtcag gcccttattt tcaagaaact gaggaatttt ctttgtgtag     3943
ctttgctctt tggtagaaaa ggctaggtac acagctctag acactgccac acagggtctg     4003
caaggtcttt ggttcagcta agctaggaat gaaatcctgc ttcagtgtat ggaaataaat     4063
gtatcataga aatgtaactt ttgtaagaca aaggttttcc tcttctattt tgtaaactca     4123
aaatatttgt acatagttat ttatttattg gagataatct agaacacagg caaaatcctt     4183
gcttatgaca tcacttgtac aaaataaaca aataacaatg tgctctcggg ttgtgtgtct     4243
gttcattttc ctccctcagt gccctcattt tatgtcatta aatggggctc acaaaccatg     4303
caaatgctat gagatgcatg gagggctgcc ctgtacccca gcacttgtgt tgtctggtga     4363
tggcaccatc tctgattttc aaagcttttt ccagaggcta ttattttcac tgtagaatga     4423
tttcatgcta tctctgtgtg cacaaatatt tattttcttt ctgtaaccat aacaacttca     4483
tatatgagga cttgtgtctc tgtgctttta aatgcataaa tgcattatag gatcatttgt     4543
tggaatgaat taaataaacc cttcctgggg catctggcga atcccagctg                4593
```

<210> SEQ ID NO 2
<211> LENGTH: 575
<212> TYPE: PRT
<213> ORGANISM: Homo sapiens

<400> SEQUENCE: 2

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160
```

-continued

```
Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
        290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
                340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
        370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
        450                 455                 460

Ile Cys Gly Pro Asp Ser Ala Leu Val Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Ala Val Gly Leu
                500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575
```